United States Patent
Merchant et al.

(10) Patent No.: US 9,867,918 B2
(45) Date of Patent: Jan. 16, 2018

(54) CARTRIDGES USEFUL IN CLEANING DIALYSIS SOLUTIONS

(71) Applicant: Fresenius Medical Care Holdings, Inc., Waltham, MA (US)

(72) Inventors: Stephen A. Merchant, Oklahoma City, OK (US); Kerissa Adams, Norman, OK (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 339 days.

(21) Appl. No.: 14/656,729

(22) Filed: Mar. 13, 2015

(65) Prior Publication Data

US 2015/0258266 A1 Sep. 17, 2015

Related U.S. Application Data

(60) Provisional application No. 61/954,161, filed on Mar. 17, 2014.

(51) Int. Cl.
*A61M 1/16* (2006.01)
*A61M 1/28* (2006.01)
(Continued)

(52) U.S. Cl.
CPC ........ *A61M 1/1696* (2013.01); *A61M 1/1656* (2013.01); *A61M 1/287* (2013.01); *B01J 20/0211* (2013.01); *B01J 20/0292* (2013.01); *B01J 20/043* (2013.01); *B01J 20/06* (2013.01); *B01J 20/08* (2013.01); *B01J 20/20* (2013.01); *B01J 20/28052* (2013.01); *B01J 39/12* (2013.01); *A61M 2205/02* (2013.01); *B01J 2220/62* (2013.01)

(58) Field of Classification Search
CPC .. A61M 1/1656; A61M 1/1696; A61M 1/287; A61M 2205/02; B01J 20/0211; B01J 20/0292; B01J 20/043; B01J 20/06; B01J 20/08; B01J 20/20; B01J 20/28052; B01J 2220/62; B01J 39/12
See application file for complete search history.

(56) References Cited

U.S. PATENT DOCUMENTS

| 3,669,878 A | 6/1972 | Marantz et al. |
| 3,669,880 A | 6/1972 | Marantz et al. |

(Continued)

FOREIGN PATENT DOCUMENTS

| RU | 2426561 C2 | 8/2011 |
| RU | 2011102164 A | 7/2012 |

(Continued)

OTHER PUBLICATIONS

International Search Report and Written Opinion issued in corresponding International Patent Application No. PCT/US2015/020311, dated Sep. 2, 2015 (16 pages).

(Continued)

*Primary Examiner* — John Kim
(74) *Attorney, Agent, or Firm* — Kilyk & Bowersox, P.L.L.C.

(57) ABSTRACT

Cartridges useful in regenerating or purifying dialysis solutions are described as well as methods to regenerate or purify spent dialysis solutions. Dialysis methods using the sorbent cartridges of the present invention are further described.

60 Claims, 6 Drawing Sheets

(51) Int. Cl.
*B01J 20/20* (2006.01)
*B01J 20/02* (2006.01)
*B01J 39/12* (2006.01)
*B01J 20/28* (2006.01)
*B01J 20/08* (2006.01)
*B01J 20/06* (2006.01)
*B01J 20/04* (2006.01)

(56) References Cited

U.S. PATENT DOCUMENTS

| | | | |
|---|---|---|---|
| 3,697,410 | A | 10/1972 | Johnson et al. |
| 3,697,418 | A | 10/1972 | Johnson |
| 3,703,959 | A | 11/1972 | Raymond |
| 3,850,835 | A | 11/1974 | Marantz et al. |
| 3,989,622 | A | 11/1976 | Marantz et al. |
| 3,989,625 | A | 11/1976 | Mason |
| 4,025,608 | A | 5/1977 | Tawil et al. |
| 4,213,859 | A | 7/1980 | Smakman et al. |
| 4,256,718 | A | 3/1981 | McArthur et al. |
| 4,360,507 | A | 11/1982 | McArthur et al. |
| 4,460,555 | A | 7/1984 | Thompson |
| 4,484,599 | A | 11/1984 | Hanover et al. |
| 4,495,129 | A | 1/1985 | Newberry et al. |
| 4,558,996 | A | 12/1985 | Becker |
| 4,560,472 | A | 12/1985 | Granzow et al. |
| D282,578 | S | 2/1986 | Humphreys et al. |
| 4,738,668 | A | 4/1988 | Bellotti et al. |
| 5,498,338 | A | 3/1996 | Kruger et al. |
| 5,597,805 | A | 1/1997 | Breborowicz et al. |
| 5,631,025 | A | 5/1997 | Shockley et al. |
| 5,641,405 | A | 6/1997 | Keshaviah et al. |
| 5,704,915 | A | 1/1998 | Melsky et al. |
| 5,782,796 | A | 7/1998 | Din et al. |
| 5,824,213 | A | 10/1998 | Utterberg |
| 5,938,634 | A | 8/1999 | Packard |
| 5,955,450 | A | 9/1999 | Breborowicz et al. |
| 5,968,966 | A | 10/1999 | Bergstrom |
| 5,980,481 | A | 11/1999 | Gorsuch |
| 5,984,891 | A | 11/1999 | Keilman et al. |
| 6,017,942 | A | 1/2000 | Bergstrom |
| 6,074,359 | A | 6/2000 | Keshaviah et al. |
| 6,117,122 | A | 9/2000 | Din et al. |
| 6,146,536 | A | 11/2000 | Twardowski |
| 6,196,992 | B1 | 3/2001 | Keilman et al. |
| 6,274,103 | B1 | 8/2001 | Taylor |
| 6,284,131 | B1 | 9/2001 | Hogard et al. |
| 6,284,139 | B1 | 9/2001 | Piccirillo |
| 6,293,921 | B1 | 9/2001 | Shinmoto et al. |
| 6,299,769 | B1 | 10/2001 | Falkvall et al. |
| 6,306,836 | B1 | 10/2001 | Martis et al. |
| 6,309,673 | B1 | 10/2001 | Duponchelle et al. |
| 6,627,164 | B1 | 9/2003 | Wong |
| 6,878,283 | B2 | 4/2005 | Thompson |
| 7,033,498 | B2 | 4/2006 | Wong |
| 7,241,272 | B2 | 7/2007 | Karoor et al. |
| 8,012,118 | B2 | 9/2011 | Curtin et al. |
| 8,343,346 | B2 | 1/2013 | Crnkovich et al. |
| 8,366,921 | B2 | 2/2013 | Beden et al. |
| 8,475,399 | B2 | 7/2013 | Fulkerson |
| 8,500,994 | B2 | 8/2013 | Weaver et al. |
| 8,580,112 | B2 | 11/2013 | Updyke et al. |
| 8,597,505 | B2 | 12/2013 | Fulkerson et al. |
| 8,663,463 | B2 | 3/2014 | Weaver et al. |
| 2002/0112609 | A1 | 8/2002 | Wong |
| 2006/0140840 | A1 | 6/2006 | Wong |
| 2010/0078387 | A1 | 4/2010 | Wong |
| 2010/0217181 | A1 | 8/2010 | Roberts et al. |
| 2012/0234762 | A1 | 9/2012 | Wong |
| 2013/0190168 | A1* | 7/2013 | Wong ............... B01J 20/06 502/308 |
| 2015/0144542 | A1* | 5/2015 | Pudil ............... B01D 15/203 210/87 |

FOREIGN PATENT DOCUMENTS

| | | |
|---|---|---|
| WO | 2009157877 A1 | 12/2009 |
| WO | 2012057941 A2 | 5/2012 |

OTHER PUBLICATIONS

International Preliminary Report on Patentability issued in corresponding International Patent Application No. PCT/US2015/020311, dated Sep. 29, 2016 (11 pages).
COBE Renal Care, Inc., "Guide to Custom Dialysis," Product No. 306100-005, Revision E, Sep. 1993, pp. 1-52 (54 pages).
COBE Renal Care, Inc., "Sorbent Dialysis Primer," Product No. 306100-006, Edition 4, Sep. 1993, pp. 1-46 (56 pages).
Communication Relating to the Results of the Partial International Search issued in corresponding International Patent Application No. PCT/US2015/020311 dated Jun. 16, 2015 (7 pages).
Ash, "Sorbent Dialysis Systems: An Expert Commentary by Stephen R. Ash, MD, FACP," http://www.medscape.com/viewarticle/576534_print, Aug. 5, 2008 (11 pages).
Sung et al., "A Procedure for Purifying Jack Bean Urease for Clinical Use," Database Biosis (Online), Biosciences Information Service, Philadelphia, Pennsylvania, US, 1989, (1 page) (Abstract).
Decision on Grant received in corresponding Russian Patent Application No. 2016137126 dated Jun. 28, 2017 with English translation (24 pages).

* cited by examiner

CARTRIDGES USEFUL IN CLEANING DIALYSIS SOLUTIONS

This application claims the benefit under 35 U.S.C. § 119(e) of prior U.S. Provisional Patent Application No. 61/954,161, filed Mar. 17, 2014, which is incorporated in its entirety by reference herein.

BACKGROUND OF THE INVENTION

The present invention relates to cartridges such as ion exchange cartridges or adsorption cartridges which are useful, for instance, in dialysis. In particular, the present invention relates in general to the regeneration or purification of used dialysate fluids. The present invention further relates to methods of conducting dialysis using certain cartridges.

Dialysis is a treatment that removes the waste products and excess fluid that accumulate in the blood as a result of kidney failure. Chronic renal failure is when the renal function has deteriorated to about 25% of normal. This amount of deterioration causes significant changes in the blood chemistry and is about the time that people feel poorly enough that they seek medical care. If medical treatment is sought at that time, progression can be slowed. Late stage chronic renal failure is when kidney function has decreased to 15%. End stage renal failure is when kidney function is at 5% of normal. Death will most likely result without treatment at this point. There are approximately as many patients yearly who experience acute renal failure as with chronic renal failure, approximately ½ of these acute patients need medical treatment. On the whole, acute patients are more ill and less stable than chronic patients. They are frequently treated in ICU or CCU units of a hospital and cannot be moved. Acute patients may not survive, or may recover kidney function, or may become chronic dialysis patients. There is no current cure for renal disease. However, one treatment is transplantation, which is where a human kidney is surgically placed in the body and connected to the bladder. Daily medication is needed to keep the body from rejecting the transplanted kidney. Also, there is peritoneal dialysis (PD). With this treatment, a mild saltwater solution containing dextrose and electrolytes called dialysate is put into the peritoneal cavity. Because there is a rich blood supply to this abdominal cavity, urea and other toxins from the blood and fluid are moved into the dialysate, thereby cleaning the blood. The dialysate is then drained from the peritoneum. Later "fresh" dialysate is again put into the peritoneum.

Also, there is hemodialysis. This is a method of blood purification in which blood is continually removed from the body during a treatment session and passed through a dialyzer (artificial kidney) where metabolic waste and excess water are removed and pH and acid/base balances are normalized. The blood is simultaneously returned to the body. The dialyzer is a small disposable device consisting of a semi-permeable membrane. The membrane allows the wastes, electrolytes, and water to cross but restricts the passage of large molecular weight proteins and blood cells. Blood is pumped across one side of the membrane as dialysate is pumped in the opposite direction across the other side of the membrane. The dialysate is highly purified water with salts and electrolytes added. The machine is a control unit which acts to pump and control pressures, temperatures, and electrolyte concentrations of the blood and the dialysate. The average length of one hemodialysis treatment is 3-5 hours.

There are several types of hemodialysis:

a) Single Pass—hemodialysis is the most common treatment for renal disease. Most hemodialysis treatments are performed with single pass dialysis machines. They are called single pass because the dialysate (cleaning solution) passes by the blood in the dialyzer one time and then is disposed. Single pass dialysis machines generally require:
1) a water source capable of delivering at least 1000-1500 ml/min (assuming a 50% rejection rate by the R.O. system)
2) a water purification system sufficient of providing a continuous flow of 500-800 ml/min of purified water.
3) an electrical circuit of at least 15 amps in order to pump and heat 500-800 ml of water/min.
4) a floor drain or any other receptacle capable of accommodating at least 500 ml of used dialysate/minute as well as the rejected water from the R.O. system.

b) Sorbent Dialysis—does not require a continuous water source, a separate water purification machine or a floor drain because it continuously regenerates a small volume of dialysate and incorporates a water treatment system within the machine. Therefore, sorbent systems are truly portable.
1) sorbent systems require only a 5 amp electrical source because they recycle the same small volume of dialysate throughout the dialysis procedure. The heavy duty dialysate pumps and heaters used for large volumes of dialysate in single pass dialysis are not needed.
2) the sorbent system can use 6-12 liters of tap water from which dialysate is made for an entire treatment.
3) the sorbent system uses a sorbent cartridge—which acts both as a water purifier and as a means to regenerate used dialysate into fresh dialysate. The infusate system acts with it to properly balance the electrolyte composition of the regenerated dialysate.

The sorbent cartridge containing zirconium phosphate (ZrP) and hydrous zirconium oxide (HZO) ion-exchange materials has been historically used for the REDY regeneration hemodialysis system. The scheme of the REDY cartridge is shown in FIG. 1. The sorbent cartridge is shown with the inlet and the outlet identified as numeral 11 and numeral 13, respectively. FIG. 2 shows various functions of each layer in a REDY cartridge.

The principle of the REDY cartridge is based on the hydrolysis of urea to ammonium carbonate by the enzymatic reaction of urease. The following equation shows a reaction for urea conversion to ammonia in the presence of urease:

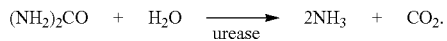

$$(NH_2)_2CO + H_2O \xrightarrow{\text{urease}} 2NH_3 + CO_2.$$

The ammonia and ammonium ions are then removed by the zirconium phosphate in exchange for the hydrogen ions and $Na^+$ ions, which are counter-ions in the cation exchanger. Zirconium phosphate also serves as cation exchanger to remove Ca, Mg, K, and all toxic metals in dialysate, thus allowing a balance of electrolyte level in the patient's blood (Ca, Mg, K) to be maintained by using an infusate system, as well as providing safety for dialysis treatment with regard to water quality. The carbonate from the urea hydrolysis then combines with the hydrogen ions in zirconium phosphate to form bicarbonate, which is delivered to the uremic patient as a base to correct for acidosis. Zirconium phosphate can be represented as inorganic cation exchange material with the molecular structure as shown below:

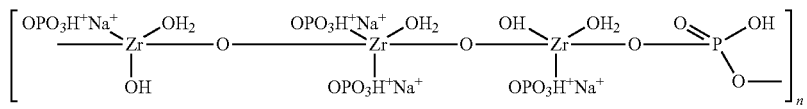

As shown, the material contains both H⁺ and Na⁺ as counterions, which are responsible for ion exchange. The relative content of these ions can be controlled by the pH to which acid ZrP (or H⁺ZrP) is titrated with NaOH. The composition of the resultant product of titration, $Na_x^+H_{2-x}^+ZrP$ (or abbreviated as "NaHZrP" herein), may vary during ion exchange processes in dialysate. The hydrous zirconium oxide (HZO) containing acetate (HZO.Ac) as a counter ion serves as an anion exchanger to remove phosphate. The material also prevents leaching of phosphate from NaHZrP and removes toxic anions (e.g., fluoride) in water that may cause harm to a patient during dialysis. The acetate released during ion exchange is also a base to correct for acidosis by acetate metabolism. The compositional formula of hydrous zirconium oxide (HZO) can be $ZrO_2 \cdot nH_2O$ (i.e. zirconium oxide hydrate) or $ZrO_2 \cdot nOH \ldots H^+An^-$ in the anion form wherein An is an anion attached to HZO, such as acetate ("Ac"), chloride, etc. Without the anion, it can be considered as partially oxalated zirconium hydroxide with various degrees of $O^{2-}$, $OH^-$ and $H_2O$ bonded to Zr, i.e., $Zr(OH)_xO_y(H_2O)_z$. The granular activated carbon in the cartridge is used in the REDY cartridge for the removal of creatinine, uric acid, and nitrogenous metabolic waste of the patient as well as chlorine and chloramine from water. Thus the REDY regenerative dialysis system is efficient to provide both safety and simplicity of water treatment and hence convenience for hemodialysis. The efficacy and safety record of the system has been well established. Nevertheless, there have been significant technological advancements in dialysis treatments as a whole, and thus, a new and improved cartridge is required to meet the needs of today's dialysis systems.

Sorbent cartridge designs would be preferred that can further reduce or prevent release of organic impurities, sodium, zirconium ions such as from zirconium phosphates, acetate ions such as from HZO.Ac, and the like, from components of a sorbent cartridge to dialysate. Accordingly, in the area of dialysis, it would be beneficial to overcome one or more of the above-described disadvantages.

SUMMARY OF THE PRESENT INVENTION

A feature of the present invention is to provide materials which are useful in the regeneration or purification of solutions containing waste products.

A further feature of the present invention is to provide materials which are useful in the regeneration or purification of dialysis solutions such as hemodialysis or peritoneal dialysis solutions or other dialysate solutions.

A further feature of the present invention is to provide a sorbent cartridge for regenerating or purifying spent dialysis fluid which can reduce organic impurity release into dialysate.

A further feature of the present invention is to provide methods to regenerate or purify spent dialysis fluids which can use such sorbent cartridges.

A further feature of the present invention is to provide dialysis systems which can regenerate or purify spent dialysis fluids with such sorbent cartridges.

A further feature of the present invention is to provide a sorbent cartridge for regenerating or purifying spent dialysis fluid which can provide cartridge improvement with respect to at least one of 1) reduce or eliminate acetate content and release, 2) reduce zirconium release, 3) reduce sodium release, 4) increase cartridge effluent pH, 5) reduce $pCO_2$, 6) reduce impurities (e.g., total organic carbon (TOC)) in regenerated dialysate, 7) improve bicarbonate dynamics, 8) maintain urea and phosphate capacity, or any combination of 1), 2), 3), 4), 5), 6), 7) and/or 8) including all of 1)-8) or any lesser included combination thereof. A further feature of the present invention is to provide a sorbent cartridge which can meet one or more of these improvements 1)-8) and function well with required dialysis treatment performance parameters.

Another feature of the present invention is to provide a sorbent cartridge which includes hydrous zirconium chloride (HZO-Cl⁻) that can eliminate acetate content and release, increase or maintain alkalinity, and/or reduce or control soluble Zr within tolerances.

Another feature of the present invention is to provide a sorbent cartridge which includes zirconium phosphate with increased sodium loading and hydrous zirconium oxide-chloride that can eliminate acetate content and release, and increase or maintain alkalinity, reduce or control soluble Zr within tolerances.

Another feature of the present invention is to orient or arrange the sorbents within the cartridge as a function of physical properties, not chemical properties, wherein high surface area ZP and ZO can be arranged in a way so as to make the most use of them while standard ZP and ZO would be used to make the best use of them. This can result in a more efficient sorbent device. In addition to surface area, particle size is a physical property that can be used to arrange sorbents.

A further feature of the present invention is to provide a sorbent cartridge for regenerating or purifying spent dialysis fluid that provides sorbent layers configured for superior and efficient purification.

An additional feature of the present invention is to overcome one or more of the above-described difficulties.

Additional features and advantages of the present invention will be set forth in part in the description which follows, and in part will be apparent from the description, or may be learned by practice of the present invention. The objectives and other advantages of the present invention will be realized and obtained by means of the elements and combinations particularly pointed out in the written description and appended claims.

To achieve these and other advantages and in accordance with the purposes of the present invention, the present invention relates to a sorbent cartridge that comprises (from inlet to outlet) a) a first carbon-containing layer; b) an enzyme-comprising layer, for instance, a layer comprising urease that follows the first carbon-containing layer within the sorbent cartridge; c) a second carbon-containing layer that follows the enzyme-comprising layer within the sorbent cartridge; d) a zirconium phosphate-containing layer that follows the second carbon-containing layer within the sorbent cartridge; e) a hydrous zirconium oxide-comprising layer that follows the zirconium phosphate-containing layer; and f) a (bi)carbonate layer that follows the hydrous zirconium oxide layer comprising sodium (bi)carbonate.

The present invention further relates to a sorbent cartridge that comprises (from inlet to outlet) a) a first carbon-containing layer; b) an enzyme-containing layer, for instance, a layer comprising urease that follows the first carbon-containing layer within the sorbent cartridge; c) a second carbon-containing layer that follows the enzyme-containing layer within the sorbent cartridge; d) a zirconium phosphate-containing layer that follows the second carbon-containing layer within the sorbent cartridge, wherein the zirconium phosphate-containing layer comprises sodium loading of greater than 55 mg Na/g zirconium phosphate; e) a hydrous zirconium oxide layer that follows the zirconium phosphate-containing layer, said layer comprising hydrous zirconium oxide-chloride that has alkaline pH; and f) a (bi)carbonate layer that follows the hydrous zirconium oxide layer comprising sodium (bi)carbonate.

The present invention also relates to a method to regenerate or purify spent dialysis fluid comprising passing spent dialysis fluid through one of the sorbent cartridges described herein.

The present invention further relates to a dialysis system to regenerate or purify spent dialysis fluid comprising one of the sorbent cartridges described herein.

The present invention also relates to a sorbent cartridge that can include a housing, a first sorbent layer, and a second sorbent layer. The housing can define a cartridge interior, the cartridge interior having a volume and configured to hold at least two layers of sorbent material. The housing can include a first end having a first port configured to permit entry of a fluid into the cartridge interior, and a second end distal to the first end and having a second port configured to permit exit of the fluid from the cartridge interior. The first sorbent layer can be situated in the cartridge interior. The first sorbent layer can have a first geometry and contain a first sorbent material. The second sorbent layer can be situated in the cartridge interior. The second sorbent layer can have a second geometry and can contain a second sorbent material. The first and second sorbent materials can have equivalent chemical compositions. The first geometry can differ from the second geometry in at least one dimension, or the first sorbent material can differ from the second sorbent material in at least one physical characteristic, or both.

The present invention also provides a sorbent cartridge having an inlet and outlet including at least a first layer and a second layer. The first layer and the second layer can contain particulate material having the same or substantially the same chemical composition. The first layer can be located closer to the inlet than the second layer. The particulate material in the first layer can have at least a greater/higher property then the particulate material in the second layer with respect to average particle size, average surface area, adsorption capacity for at least one species, or any combination thereof.

It is to be understood that both the foregoing general description and the following detailed description are exemplary and explanatory only and are intended to provide a further explanation of the present invention, as claimed.

The accompanying drawings, which are incorporated in and constitute a part of this application, illustrate several embodiments of the present invention and together with the description, serve to explain the principles of the present invention.

DETAILED DESCRIPTION OF THE PRESENT INVENTION

Figure 1:
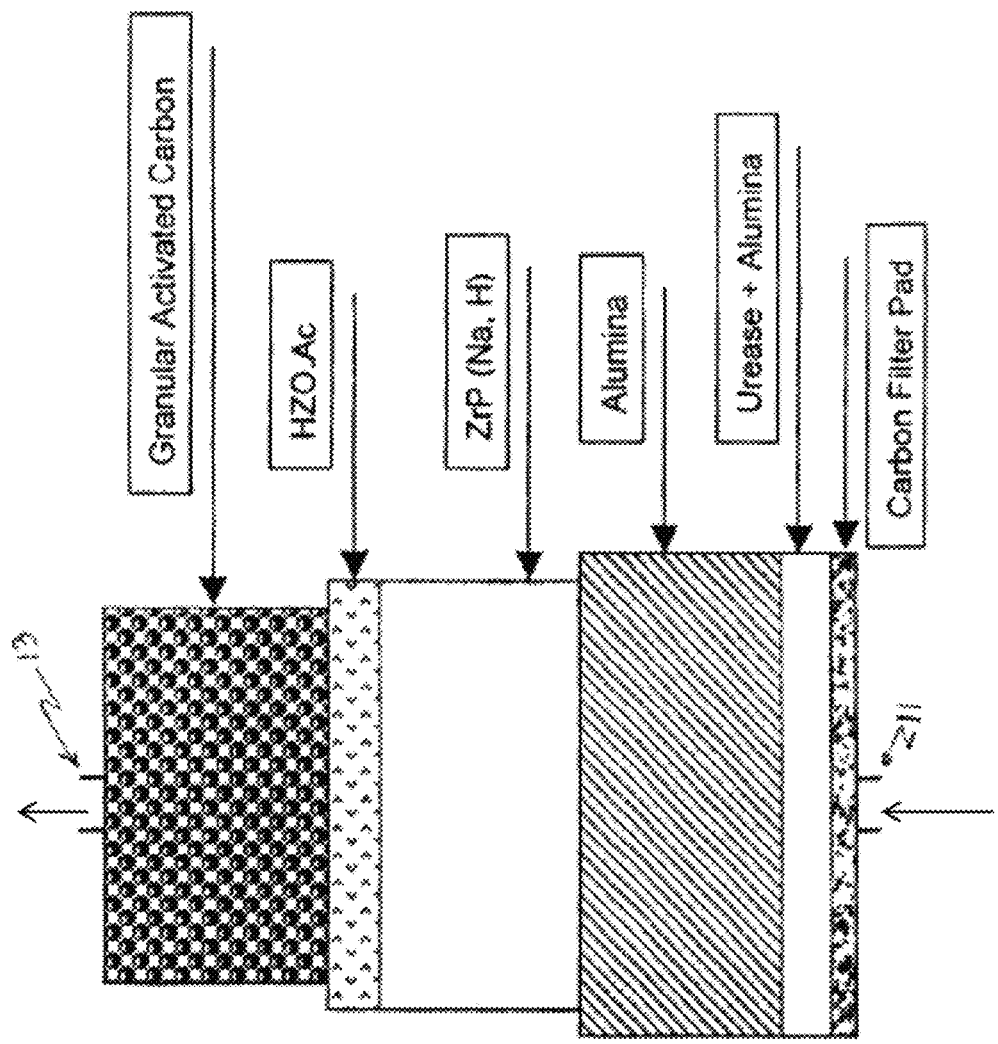
FIG. 1 is a schematic diagram showing a REDY® cartridge.
Figure 2:
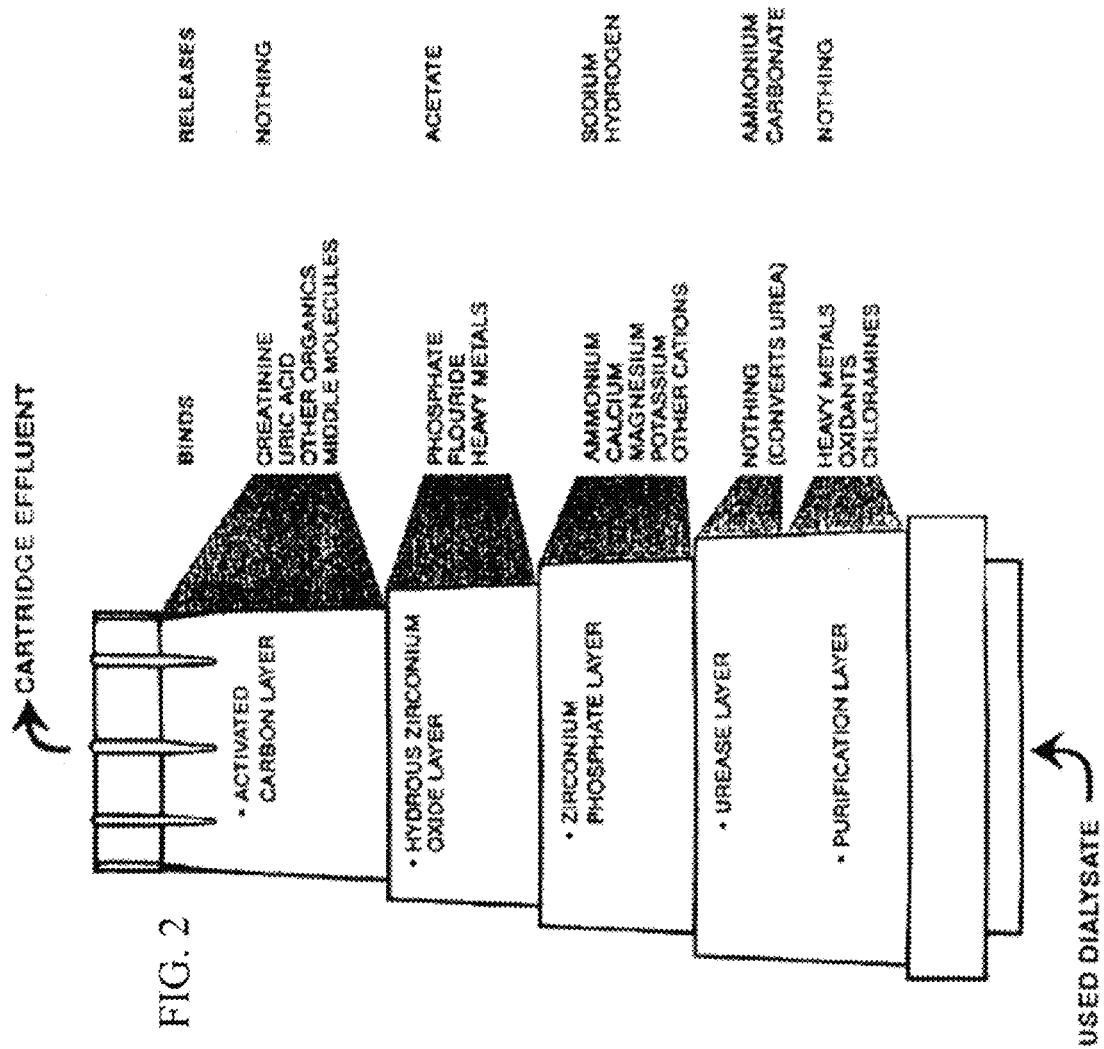
FIG. 2 is a diagram showing a cartridge and the various functions of each layer in a REDY® cartridge.

The present invention relates to materials useful for separation processes such as the removal of waste products and excess fluid that accumulates in dialysate fluids. These materials can be present in a container (i.e., a cartridge) capable of holding the materials useful for the separation process. As an option, the materials described in detail below or the arrangement of various materials can be used in a dialysis system or other similar type of system that is useful for the removal of waste products and/or excess fluid that accumulates in dialysate fluids, for instance, as a result of conducting dialysis. As described in more detail below, the present invention is useful in purifying or regenerating dialysate fluids used in peritoneal dialysis (PD) and in hemodialysis (HD). For purposes of the present invention, a dialysis solution means a peritoneal dialysis solution or dialysate fluids that are useful in hemodialysis or sorbent dialysis systems. Conventional dialysis solutions for PD or HD can be used and regenerated by the present invention and are known to those skilled in the art.

The sorbent cartridge(s) of the present invention is preferably comprised of layers of highly specified and designed materials, and performs the regenerative function by employing three chemical phenomena: (i) adsorption, (ii) catalysis, and (iii) ion exchange. Adsorption describes the immobilization or fixation of mobile species at a solid interface or surface. Catalysis is a process by which the rate of a chemical reaction is increased by the reduction of the reaction activation energy via a component in the reaction whose net rate of consumption is zero. Ion exchange is a process in which particular solid materials adsorb species for which they have a high affinity and in turn release a species for which its affinity is lower.

The present invention, in part, relates to a sorbent cartridge that includes dialysate treatment components of carbon, a urease source, zirconium phosphate ("ZP"), zirconium oxide, and (bi)carbonate.

The layers of materials in a cartridge of the present invention can be situated in the following preferred layer arrangement with these preferred materials from inlet to outlet:

Activated Carbon Layer (inlet)—adsorbs organic species, other lower polarity species such as oxidants and various heavy metal complexes emanating from both the water source and the patient.

Enzyme/Enzyme Retention Layer—the enzyme urease catalyzes the hydrolysis (hydrolytic decomposition) of aqueous urea to form bicarbonate and ammonium. The material used to retain or immobilize the urease can be alumina ($Al_2O_3$).

Activated Carbon Layer—performs same function as first carbon layer; in addition will adsorb organic species emanating from the enzyme source.

Zirconium Phosphate Layer—cation exchange material which adsorbs various cationic species in exchange for hydrogen and sodium ions.

Zirconium Oxide Layer—anion exchange material which adsorb various anionic species in exchange for chloride and hydroxide ions.

Sodium Bicarbonate Layer (outlet)—soluble USP grade sodium bicarbonate which dissolves upon priming the cartridge with dialysate thus increasing the concentration of sodium bicarbonate in the dialysate without directly pumping the sodium bicarbonate through the cartridge.

In sorbent dialysis, urea from the patient is transported into the dialysate at the dialyzer. Once in the dialysate, the urea is pumped to the sorbent cartridge where it is hydrolyzed into ammonium and bicarbonate ions. Due to this constant generation of bicarbonate in the dialysate for the duration of the dialysis treatment, the initial concentration of bicarbonate in the dialysate is typically lower in comparison to a normal single-pass dialysis treatment. This initial lower concentration prevents excessive bicarbonate in the dialysate as the treatment progresses, and thus prevents alkalosis. There are two features which have classically made this low initial bicarbonate paradigm safe: (1) a transient low concentration due to the dynamics of the system (not a constant, long duration exposure of low bicarbonate dialysate to a patient); and (2) the low volume ratio of dialysate to patient which inherently prevents the dialysate from driving the patient chemistries.

Compensation for this initial period of low dialysate bicarbonate in sorbent dialysis has classically involved the use of a large concentration of acetate ion donated by the sorbent cartridge which is transported to the patient (gradient driven) and converted to bicarbonate in the liver, thus preventing acidotic symptoms.

However, with the present invention, in the preferred design, there is no acetate in the sorbent cartridge. All of the buffer emanating from the cartridge is in the form of bicarbonate. Instead of the sorbent cartridge donating an initial bolus of acetate, the cartridge donates an initial bolus of sodium bicarbonate.

Cartridge designs of the present invention provide bicarbonate initially to compensate for the period of lower bicarbonate and allows for a bicarbonate-only total buffer paradigm. Elimination of acetate from the cartridge, and thus the dialysate, a) simplifies the total buffer characterization, and/or b) eliminates potential complications due to acetate intolerance (high initial acetate concentrations coupled with new high flux/high flow rate dialysis), and/or c) eliminates potential alkalosis symptoms due to lack of understanding of the acetate-bicarbonate dynamic.

To reduce acetate, increase or maintain alkalinity, and/or reduce or control soluble Zr within tolerances, a series of layers can be used in the sorbent cartridge which includes a hydrous zirconium oxide layer of hydrous alkaline oxide-chloride that has an alkaline pH, and a (bi)carbonate layer, near or at the effluent outlet end of the cartridge.

A sorbent cartridge of the present invention can include a hydrous zirconium oxide layer that is hydrous zirconium oxide-chloride (HZO•Cl) having an alkaline pH. The formula for the HZO•Cl can be as in the Background above. To eliminate acetate, increase or maintain alkalinity, and/or reduce or control soluble zirconium within tolerances, HZO-Cl can be provided in the cartridge design. This HZO-Cl layer can be used without sodium zirconium carbonate. Alkaline pH of the HZO-Cl can reduce infused chloride or at least control it to a tolerable level, and can reduce soluble Zr discharge from the cartridge. Increasing alkaline pH can provide greater reductions in infused chloride, soluble Zr, or both. The HZO-Cl layer of alkaline pH can be used in combination with a (bi)carbonate layer that follows the hydrous zirconium oxide layer. The (bi)carbonate layer can comprise sodium carbonate ($Na_2CO_3$), sodium bicarbonate ($NaHCO_3$), or both, at the effluent end of the cartridge.

The hydrous zirconium oxide-chloride can have a pH greater than about 8, or greater than about 9, or about 9.5 to about 10.5, or about 10, or other alkaline values. The pH of the HZO-Cl generally increases with smaller relative proportions of chloride in the HZO-Cl. The chloride content in mg per g of HZO-Cl can be, for example, from about 25 mg/g to about 10 mg/g, or any amount that provides an alkaline pH.

With the cartridge design of the present invention, one or more advantages, improvements, and/or properties can be achieved, especially compared to conventional cartridges. With the present invention, it is possible to eliminate acetate content in the sorbent cartridge. In other words, the acetate content in the sorbent cartridge can be 0 wt % or about 0 wt % with respect to any layer and the entire sorbent cartridge. With the present invention, and the design of the chemistry and layers, the sorbent cartridge has the ability to operate with high dialysate flow rates and/or has the ability to operate with high flux dialyzers and thus have shorter treatment times (e.g., approximately four hours+/−30 minutes). For instance, with the present invention, dialysate flow rates can be from about 300 to about 500 ml/min. With the use of faster dialysis solution flow rates, this increases the efficiency of diffusion of urea from blood to dialysate. The cartridge design of the present invention makes this possible. The present invention also has the ability to reduce TOC (total organic carbon) release to levels that are quite acceptable.

The present invention provides sorbent cartridge designs that can improve control and balancing of sodium in dialysate and to the patient with dialysate pH and bicarbonate levels. As indicated, zirconium phosphate has finite available ion exchange sites. Initially all sites can contain hydrogen. Neutralization of zirconium phosphate exchanges some hydrogen for sodium. In the cartridge, sites exchange sodium and hydrogen for $NH_4^+$ and cations. Too much sodium on zirconium phosphate can lead to too much sodium in dialysate. Too much hydrogen on zirconium phosphate can lead to low pH dialysate, low bicarbonate, and acidosis. Sorbent cartridges of the present invention can provide a better balancing of these factors and outcome.

A sorbent cartridge is provided in the present invention that can reduce or prevent donation of organic impurities, and/or metal ions. A sorbent cartridge of the present invention can have layers of carbon positioned both before and after a layer comprising a urease source, such as for example of Jack Bean meal, in advance of a first layer of zirconium phosphate within the sorbent cartridge. For example, a layer comprising Jack Bean meal layer material can be located between two separate carbon layers in a sorbent cartridge that includes zirconium phosphate without a layer zirconium phosphate being present between either of the carbon layers and the Jack Bean meal layer. The carbon layer can be, for example, a layer of granulated carbon, or a carbon filter pad, or other carbon materials through which dialysate can flow for treatment before and after a Jack Bean meal layer. The Jack Bean meal layer optionally can be supported or immobilized, such as with alumina or other suitable or known immobilizing agents. Further, an alumina backup layer optionally can be included between the Jack Bean meal layer and the carbon layer that follows the Jack Bean meal layer. This cartridge design can significantly reduce the presence of organic impurities, released metal ions such as sodium ions, zirconium ions, or any combinations of these, in dialysates that are regenerated or purified in the sorbent cartridge. The indicated sequence of the separate carbon layers, Jack Bean meal, and zirconium phosphate layer can provide unexpectedly enhanced capture of impurities and/or released metal ions as compared to merely locating an activated carbon layer or carbon filter pad at the inlet and/or outlet of a sorbent cartridge.

The order and composition of layers for a cartridge design of the present invention prior to be used to regenerate or purify spent dialysis fluid, can be, for example, as follows (e.g., top (exit or outlet) to bottom (entrance-inlet) in the cartridge):

a) one or more layers comprising, consisting essentially of, consisting of, or including sodium bicarbonate (e.g., 20 g to about 30 g), b) one or more layers comprising, consisting essentially of, consisting of, or including hydrous zirconium oxide-hydroxide and/or hydrous zirconium oxide-chloride (e.g., 150 g to about 250 g), c) one or more layers comprising, consisting essentially of, consisting of, or including zirconium phosphate (e.g., 650 g to about 1800 g), for instance, with a sodium loading of from about 50 mg to about 56 mg Na/g zirconium phosphate (the zirconium phosphate can have the formula as set forth in the Background above), d) one or more layers comprising, consisting essentially of, consisting of, or including a carbon layer or pad (e.g., about 50 g to about 500 g carbon), e) optionally one or more layers comprising, consisting essentially of, consisting of, or including alumina or other like material (e.g., about 100 g to about 500 g), f) one or more enzyme containing layers, such as a layer comprising, consisting essentially of, consisting of, or including urease, for example Jack Bean meal with or without alumina blend (e.g., about 100 g to about 400 g, including from about 5 grams to about 50 grams Jack Bean meal), and g) one or more layers comprising, consisting essentially of, consisting of, or including a carbon layer or pad (e.g., about 50 g to about 500 g carbon). These amounts for components a)-g) are provided as an example, and other amounts of these materials may be used.

The order and composition of layers for a cartridge design of the present invention after being used (or after a few minutes of being used) to regenerate or purify spent dialysis fluid, can be, for example, as follows (e.g., top (exit or outlet) to bottom (entrance-inlet) in the cartridge):

a) one or more layers comprising, consisting essentially of, consisting of, or including hydrous zirconium oxide-hydroxide and/or hydrous zirconium oxide-chloride (e.g., 150 g to about 250 g), b) one or more layers comprising, consisting essentially of, consisting of, or including zirconium phosphate (e.g., 650 g to about 1800 g), for instance, with a sodium loading of from about 50 mg to about 56 mg Na/g zirconium phosphate, c) one or more layers comprising, consisting essentially of, consisting of, or including a carbon layer or pad (e.g., about 50 g to about 500 g carbon), d) optionally one or more layers comprising, consisting essentially of, consisting of, or including alumina or other like material (e.g., about 100 g to about 500 g), e) one or more enzyme containing layers, such as a layer comprising, consisting essentially of, consisting of, or including urease, for example, Jack Bean meal with or without alumina blend (e.g., about 100 g to about 400 g, including from about 5 grams to about 50 grams Jack Bean meal), and f) one or more layers comprising, consisting essentially of, consisting of, or including a carbon layer or pad (about e.g., 50 g to about 500 g carbon). These amounts for components a)-g) are provided as an example, and other amounts of these materials may be used.

As indicated earlier, with the present invention, the (bi)carbonate layer, after having spent or used dialysate fluid pass through the cartridge, will dissolve in the dialysate fluid, and disappear or essentially disappear from the cartridge as a layer.

Figure 3:
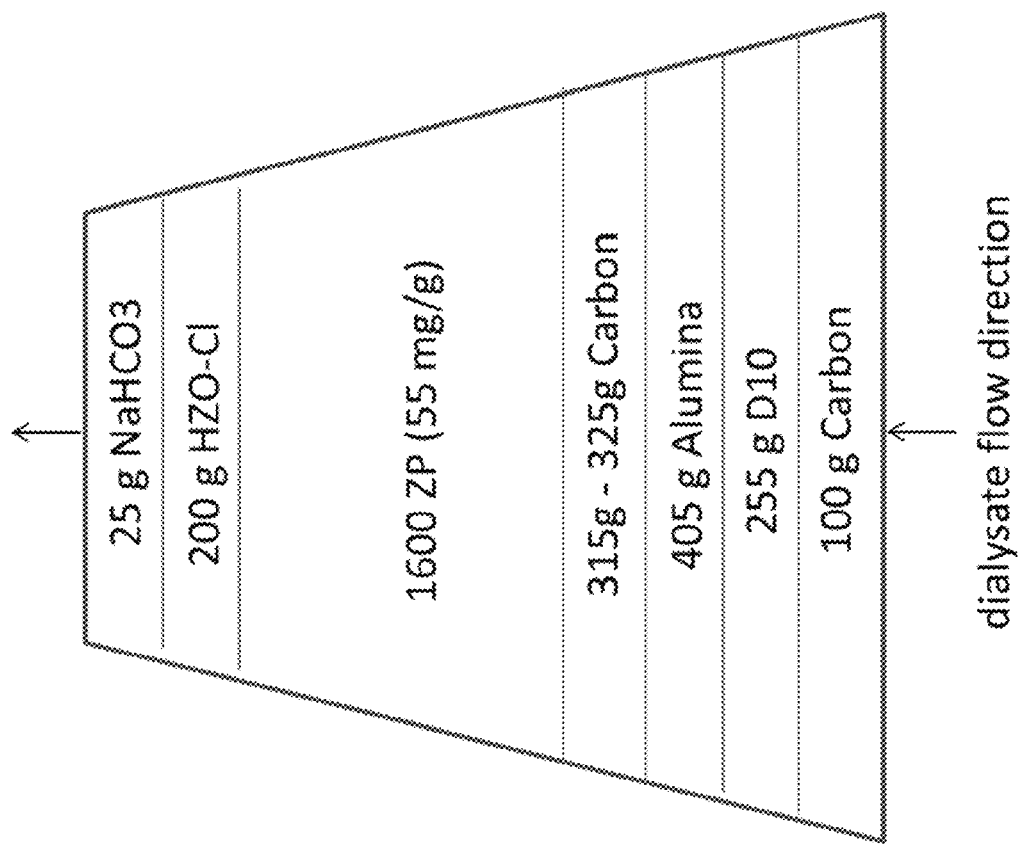
FIG. 3 is an exploded view of materials in a sorbent cartridge according to an example of the present application.

Referring to FIG. 3, the sorbent cartridge can comprises a first carbon-containing layer(s), an enzyme-containing layer(s) ("D10") comprising Jack Bean meal that follows the first carbon-containing layer within the sorbent cartridge, an optional alumina layer(s), a second carbon-containing layer(s) that follows the enzyme-containing layer and alumina layer within the sorbent cartridge, a zirconium phosphate-containing layer(s), a hydrous zirconium oxide layer(s) that follows the zirconium phosphate-containing layer comprising hydrous zirconium oxide-chloride that has alkaline pH, and sodium (bi)carbonate layer(s) that follows the hydrous zirconium oxide layer.

In the example of the sorbent cartridge of FIG. 3, sodium (bi)carbonate can be used in an amount of from about 20 g to about 30 g, or from about 22 g to about 28 g, or from about 24 g to about 26 g, or about 25 g, or other amounts. The hydrous zirconium oxide-chloride which has an alkaline pH can be used in an amount of from about 50 g to about 300 g, or from about 75 g to about 200 g, or about 100 g, or other amounts. The zirconium phosphate layer can be used in an amount of from about 650 g to about 1800 g, or from about 800 g to about 1600 g, or from about 900 g to about 1300 g, or other amounts. The zirconium phosphate of this example can have a sodium loading of greater than 55 mg/g Na/g zirconium phosphate, or from about 56 mg to about 58 mg Na/g ZP, or about 57 mg Na/g ZP, or other values. The carbon layer or pad can be used in an amount of from about 50 g to about 500 g carbon or other amounts, the alumina or other like material can be used in an amount of from about 100 g to about 500 g or other amounts, the Jack Bean meal/alumina blend can be used in amounts of from about 100 g to about 400 g, including from about 5 grams to about 50 grams Jack Bean meal or other amounts, and the bottom carbon layer or pad can be used in an amount of from about 50 g to about 500 g carbon or other amounts. Any effective amounts of the above-described materials can be present in the cartridge. These amounts (or any amounts recited herein) can be with respect to a cartridge having the following dimensions: 2 inches-3 inches diameter by 5 inches to 10 inches length, or having the following dimensions: 4 inches-6 inches diameter by 6 inches-12 inches length. However, it is to be understood that these amounts provide weight ratios for each layer with respect to each other layer so as to permit adjustments in any sized cartridge.

A sorbent cartridge can include zirconium phosphate, such as (e.g. as a layer(s)) with increased sodium loading. To eliminate acetate, increase or maintain alkalinity, and/or reduce or control soluble zirconium within tolerances, HZO-Cl can be provided in the cartridge design. This HZO-Cl layer can be used without being combined with the SZC and glass beads. The chloride content of the HZO-Cl can be proportionally reduced sufficient to provide HZO-Cl of an alkaline pH. The hydrous zirconium oxide-chloride can have a pH greater than about 8, or greater than about 9, or about 9.5 to about 10.5, or about 10, or other alkaline values. The pH of the HZO-Cl generally increases with smaller relative proportions of chloride in the HZO-Cl. The chloride content in mg per g of HZO-Cl can be, for example, from about 25 mg/g to about 10 mg/g, or any amount that provides an alkaline pH. Alkalinity may be improved slightly by an increased sodium loading in the zirconium phosphate layer. Increasing alkaline pH can provide greater reductions in infused chloride, soluble Zr, or both. The HZO-Cl layer of alkaline pH can be used in combination with a (bi)carbonate layer that follows the hydrous zirconium oxide layer comprising sodium carbonate ($Na_2CO_3$), sodium bicarbonate ($NaHCO_3$), or both, at the effluent end of the cartridge.

Figure 4:
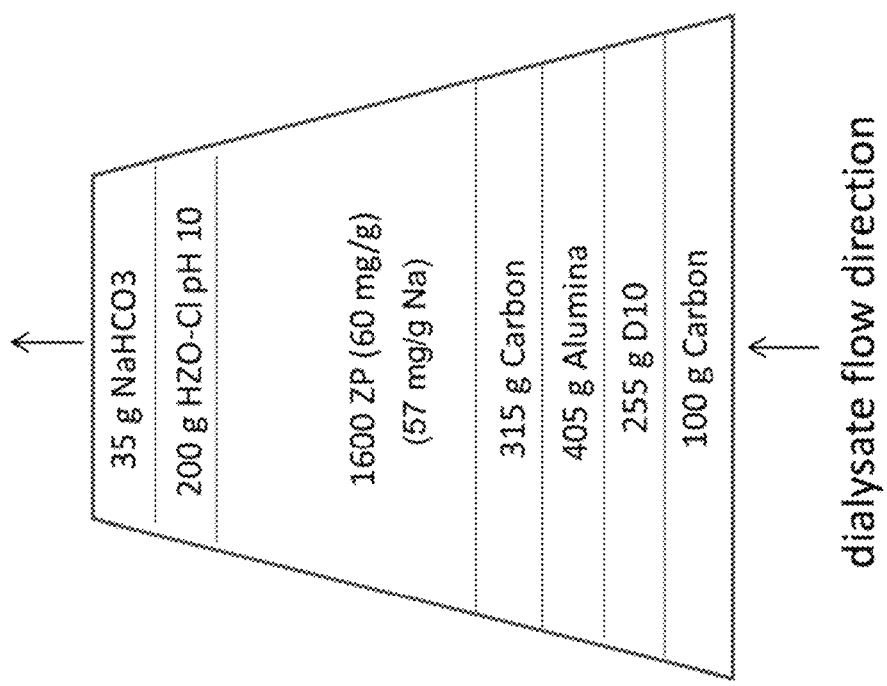
FIG. 4 is an exploded view of materials in a sorbent cartridge according to an example of the present application.
Figure 5:
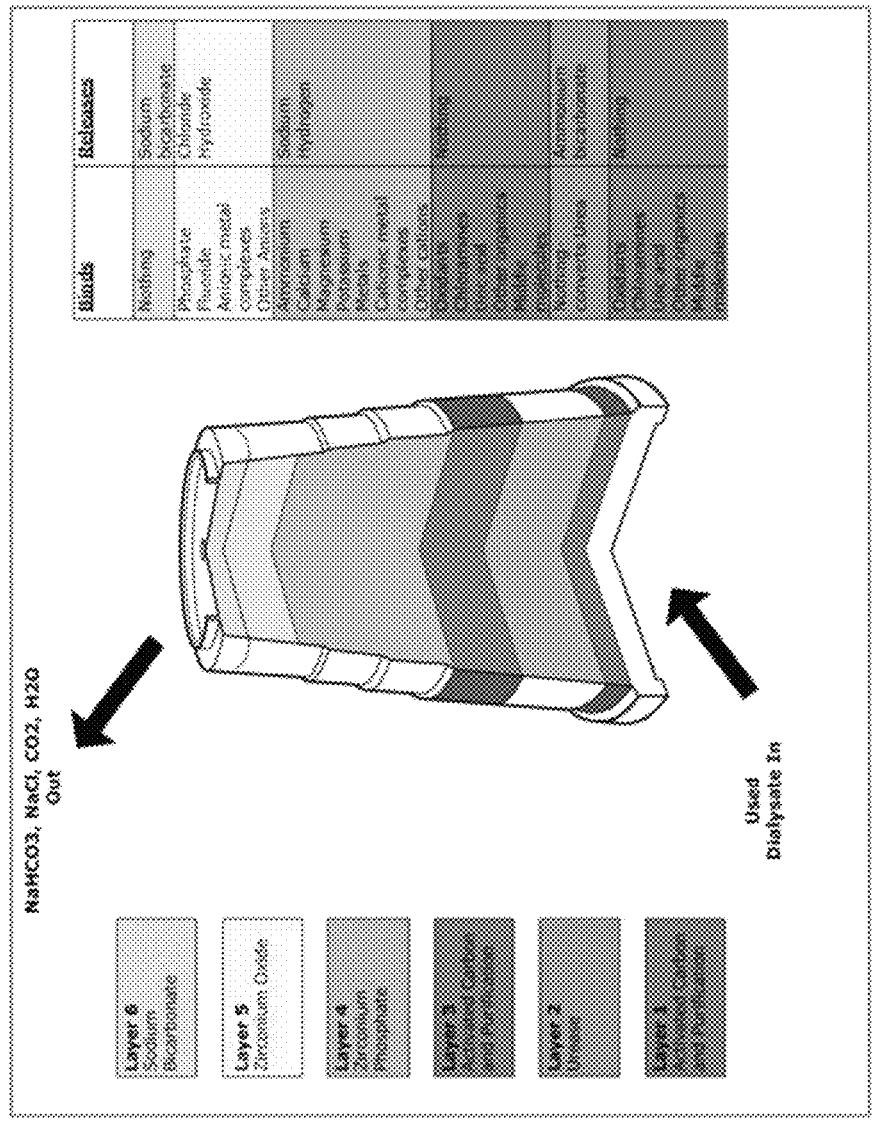
FIG. 5 is an exploded view of materials in one example of a sorbent cartridge of the present invention and the various functions of each layer.

Referring to FIG. 4, the sorbent cartridge can comprises a first carbon-containing layer, an enzyme-containing layer ("D10") comprising Jack Bean meal that follows the first carbon-containing layer within the sorbent cartridge, an optional alumina layer, a second carbon-containing layer that follows the enzyme-containing layer and alumina layer within the sorbent cartridge, a zirconium phosphate-containing layer wherein the zirconium phosphate-containing layer comprises sodium loading of greater than 55 mg Na/g zirconium phosphate, a hydrous zirconium oxide layer that follows the zirconium phosphate-containing layer comprising hydrous zirconium oxide-chloride that has alkaline pH, and sodium (bi)carbonate layer that follows the hydrous zirconium oxide layer.

In the example of the sorbent cartridge of FIG. 4, sodium (bi)carbonate can be used in an amount of from about 20 g to about 30 g, or from about 22 g to about 28 g, or from about 24 g to about 26 g, or about 25 g, or other amounts. The hydrous zirconium oxide-chloride which has an alkaline pH can be used in an amount of from about 50 g to about 300 g, or from about 75 g to about 200 g, or about 100 g, or other amounts. The zirconium phosphate layer can be used in an amount of from about 650 g to about 1600 g, or from about 800 g to about 1500 g, or from about 900 g to about 1300 g, or other amounts. The zirconium phosphate of this example can have a sodium loading of greater than 55 mg/g Na/g zirconium phosphate, or from greater than 55 mg Na/g ZP to about 62 mg/g ZP, or from about 56 mg Na/g ZP to about 61 mg/g ZP, or from about 56 mg Na/g ZP to about 60 mg Na/g ZP, or from about 56 mg Na/g ZP to about 58 mg Na/g ZP, or about 57 mg Na/g ZP, or other values. The carbon layer or pad can be used in an amount of from about 50 g to about 500 g carbon or other amounts. The alumina or other like material can be used in an amount of from about 100 g to about 500 g or other amounts. The urease/alumina blend can be used in amounts of from about 100 g to about 400 g, including from about 5 grams to about 50 grams of, for example, Jack Bean meal or other amounts. The bottom carbon layer or pad can be used in an amount of from about 50 g to about 500 g carbon or other amounts. Any effective amounts of the above-described materials can be present in the cartridge.

The carbon can be activated carbon particles that are compacted into an activated carbon filter pad. The carbon can be activated carbon particles formed into layer of the particles that can be maintained in position by adjacent layers that adjoin the opposite sides of the carbon layer within the sorbent cartridge. Filter papers, diffusor pads, and separator rings (pads) which may be used, which can have conventional designs and structures for those types of sorbent cartridge components, such as those described in U.S. Patent Application Publication Nos. 2002/0112609 and 2012/0234762, which are incorporated in their entireties by reference herein. The various layers included in the sorbent cartridge usually are permeable to dialysate so that dialysate can continuously flow through the succession of different layers within the cartridge between the inlet and outlet thereof.

The order and composition of layers of this additional example can be, for example, as follows (e.g., top (exit or outlet) to bottom (entrance-inlet) in the cartridge), wherein layers a), b), c), and f) are optional or may be replaced with other layers such as described herein:
a) sodium bicarbonate (e.g., 20 g to about 30 g),
b) hydrous zirconium oxide-hydroxide and/or hydrous zirconium oxide-chloride (e.g., 150 g to about 250 g),
c) zirconium phosphate (e.g., 650 g to about 1800 g) with a sodium loading of from about 50 mg to about 56 mg Na/g zirconium phosphate,
d) carbon layer or pad (e.g., about 50 g to about 500 g carbon),
e) optimal alumina or other like material (e.g., about 100 g to about 500 g),
f) an enzyme-containing layer such as Jack Bean meal with or without alumina blend (e.g., about 100 g to about 400 g, including from about 5 grams to about 50 grams Jack Bean meal), and
g) carbon layer or pad (e.g., about 50 g to about 500 g carbon). These amounts for components a)-g) are provided as an example, and other amounts of these materials may be used. For any, or all of a) through g), it is to be understood that each can comprise one or more layers. For instance, in layer a), this can be one or two or more layers. Carbon layers d) and g) can be the same or different from each other with respect to amount, type of carbon, morphology of the carbon, and the like.

Any effective amounts of the above-described materials can be present in the cartridges of the present invention. For instance, with respect to the total weight of immobilized Jack Bean meal as a source of urease, the immobilized Jack Bean meal can be used in an amount of from about 100 grams to about 400 grams, or from about 150 grams to about 300 grams, or from about 200 grams to about 250 grams, or other amounts. As indicated, the Jack Bean meal can be immobilized, for example, by being blended with filler or the like such as alumina. Jack Bean meal is commercially available, such as from sources such as Sigma-Aldrich. Jack Bean meal can be used in the indicated immobilized form or by itself in amount of from about 5 grams to about 100 grams, or from about 8 grams to about 50 grams, or from about 10 grams to about 30 grams, or other amounts. Generally, the urease source, such as Jack Bean meal, can be present in an amount of from about 22,000 IU or less to about 55,000 IU or more, or from about 28,000 IU to about 42,000 IU. The particle size of the Jack Bean meal can be any effective size such as about 40 mesh or less (or less than about 0.4 mm). The remainder of the immobilized Jack bean meal can be alumina only or combinations of alumina and additional materials. Alumina is commercially available, such as from sources like Alcoa. Alumina can have the formula $Al_2O_3$. A particle size for alumina can be from about 20 microns to about 120 microns, or from about 20 microns to about 40 microns. The carbon in the carbon layers can be activated carbon in any amount and can be present in each carbon layer, for example, in an amount of from about 50 grams to about 500 grams, or from about 100 grams to about 400 grams, or from about 150 grams to about 300 grams, or from about 200 grams to about 250 grams, or from about 225 grams to about 275 grams, or other amounts. As indicated, the carbon can be activated carbon, such as activated granular carbon. The activated carbon is commercially available, such as from sources like Calgon. The activated carbon can have a particle size, for example, of from 0.4 to about 1.2 mm (or 12-50 mesh sieve), or other values. An alumina backup layer optionally can be present in an amount of from about 100 grams to about 500 grams, or from about 200 grams to about 400 grams, or from about 225 grams to about 300 grams, or other values. The particle size for the alumina in a backup layer can be the same as those indicated above for the immobilized Jack Bean meal layer.

As indicated, a sorbent cartridge of the present invention can be and preferably is acetate free or substantially acetate free. For example, the cartridge can contain less than about 3 wt % total acetate based on total weight of zirconium material and total acetate, or less than about 1 wt % total acetate based on total weight of zirconium material and total acetate, or less than about 0.5 wt % total acetate based on total weight of zirconium material and total acetate, or less than about 0.1 wt % total acetate based on total weight of zirconium material and total acetate, or from 0 to about 3 wt % total acetate based on total weight of zirconium material and total acetate, or from 0 to about 2 wt % total acetate based on total weight of zirconium material and total acetate, or from 0 to about 1 wt % total acetate based on total weight of zirconium material and total acetate, or from 0 to about 0.5 wt % total acetate based on total weight of zirconium material and total acetate, or other ranges within these values. These amounts of zirconium refer to all sources of zirconium in the cartridge, and they also can be applied to any individual layer of zirconium-containing material in the cartridge.

The hydrous zirconium oxide (HZO) component for the cartridges can have the formula $Zr(OH)_4 \cdot nH_2O$. As indicated, the cartridge design of the present invention can permit this material to be used in acetate-free form or essentially-acetate-free form. Acetate-free hydrous zirconium oxide (HZO) can be prepared, for example, by following the methods such as disclosed in U.S. Patent Application Publication Nos. US 2010/0078387 A1 and US 2006/0140840 A1, which are incorporated in their entirety by reference herein.

The zirconium phosphate of the present invention can have an adsorption capacity for ammonia, $Ca^{2+}$, $Mg^{2+}$, $K^+$, and toxic heavy metals. As an option, the adsorption capacity of the zirconium phosphate can be approximately from about 20 mg $NH_4$—N/gm ZrP to about 45 mg or more $NH_4$—N/gm ZrP, and can be at least about 30 mg $NH_4$—N/gm ZrP; from about 2 mEq $Ca^{2+}$/gm ZrP to about 7 mEq $Ca^{2+}$/gm ZrP, and can be at least about 3 mEq $Ca^{2+}$/gm ZrP; from about 1 mEq $Mg^{2+}$/gm ZrP to about 5 mEq $Mg^{2+}$/gm ZrP, and can be at least about 2 mEq $Mg^{2+}$/gm ZrP; and from about 3 mEq HM/gm ZrP to about 9 mEq HM/gm ZrP, and can be at least about 6 mEq HM/gm ZrP for heavy metals (HM). Further, the zirconium phosphate can have a $Na^+$ content of from about 1.6 mEq $Na^+$/gm ZrP to about 2.7 mEq $Na^+$/gm ZrP, and can be about 2.2 mEq $Na^+$/gm and a pH of from about 5.5 to about 6. In the cartridge design, separate zirconium phosphate layers can be included which have different sodium content with respect to each other. Other pHs can be used and different $Na^+$ contents can be used with the understanding that reduced sodium loading can be used in the sorbent cartridges of the present invention. Also, the zirconium phosphate of the present invention can have a minimum leachable $PO_4^{3-}$ for the material and can be less than about 0.05 mg $PO_4^{3-}$/gm ZrP. Other amounts can be used. In addition, the zirconium phosphate can have an average grain size of from about 30 to about 40 microns and has no residual sulfate or chloride (e.g., less than 0.01%). Other amounts can be used. Furthermore, the zirconium phosphate can satisfy the ANSI/AAMI RD-5-1992 standard on extractable toxic impurities and has a pH when in water of from about 6 to about 7. Further details of the zirconium phosphate and methods of making it, for example, are described in the indicated U.S. Pat. No. 6,627,164 B2, which is incorporated in its entirety by reference herein.

The zirconium phosphate can be used in any amount, subject to practical constraints of the size of the cartridge into which it may be loaded or positioned. As an option, the amount of the zirconium phosphate is a sufficient amount to remove at least partially if not substantially or entirely all of the ammonia present in the spent fluids while providing this performance with reduced sodium loading, such as compared to the indicated previous cartridge designs.

The cartridge can include with the bicarbonate layer, a second zirconium phosphate with higher sodium loading than a first one, and a hydrous zirconium oxide-hydroxide near the effluent outlet end of the cartridge. The sodium bicarbonate can be used in an amount of from about 20 g to about 30 g, or from about 22 g to about 28 g, or from about 24 g to about 26 g, or other amounts. The second zirconium phosphate layer can be used in an amount of from about 100 g to about 600 g, or from about 400 g to about 600 g, or from about 450 g to about 550 g, or other amounts. The second zirconium phosphate layer can have a sodium loading of from about 64 mg/g ZP to about 70 mg/g ZP, or from about 65 mg/g ZP to about 69 mg/g ZP, or from about 66 mg/g ZP to about 68 mg/g ZP, or other values. The hydrous zirconium oxide-hydroxide can be used in an amount of from about 150 g to about 250 g, or from about 175 g to about 225 g, or from about 190 g to about 200 g, or other amounts. The first zirconium phosphate layer can be used in an amount of from about 650 g to about 1600 g, or from about 800 g to about 1500 g, or from about 900 g to about 1300 g, or other amounts. The first zirconium phosphate layer can have a sodium loading of from about 50 mg/g ZP to about 56 mg/g ZP, or from about 51 mg/g ZP to about 55 mg/g ZP, or from about 52 mg/g ZP to about 54 mg/g ZP, or other values.

Other materials that can also be present in the sorbent cartridge include, but are not limited to, alumina, alumina supported urease, granulated activated carbon, activated alumina, zeolites, diatomaceous earth, direct urea sorbents, and other conventional adsorbent(s), fillers, glass beads, and the like. The materials, amounts, and other optional components and/or dialysis systems described in the following patents and publications can also be used in the present application and are incorporated in their entirety by reference herein and form a part of the present application: Des. 282,578; U.S. Pat. Nos. 3,669,878; 3,669,880; 3,697,410; 3,697,418; 3,703,959; 3,850,835; 3,989,622; 3,989,625; 4,025,608; 4,213,859; 4,256,718; 4,360,507; 4,460,555; 4,484,599; 4,495,129; 4,558,996; 7,033,498 B2, and the following articles, "Guide to Custom Dialysis," Product No. 306100-005, Revision E, pages 1-54, dated September 1993 and "Sorbent Dialysis Primer," Product No. 306100-006, Edition 4, pp. 1-51, dated September 1993 of Cobe Renal Care, Inc.

A single cartridge can be used which combines all of the above-described materials. In another example, a series of cartridges can be used wherein the combination of the above-described materials can be present in one or more cartridges. For instance, urease, alumina, and split carbon layers that sandwich these two layers can be provided in a first cartridge and the remaining layers can be placed in a second cartridge, and so on. Optionally, these various indicated layers in these sequences can be divided over three different cartridges or more. As indicated, all of the materials can be provided in a single cartridge and can be arranged as distinct layers in the single cartridge. As an option, a cartridge layer can be composed of at least about 50% by weight, or at least 75% by weight, or at least about 80% by weight, or at least about 90% by weight, or at least about 95% by weight, or least about 99% by weight, or up to 100% by weight, or from about 50% to about 100% by weight, or from about 75% to about 100% by weight, or from about 90% to about 100% by weight, or from about 95% to about 100% by weight, or from about 99% to about 100% by weight, of only the material or materials indicated for use in that layer.

As an option, in addition to any carbon filter pad that may be used in providing one or both of the indicated carbon layers on each side of the enzyme containing layer, one or more filter pads can be located throughout the sorbent cartridge to ensure that the layer integrity is maintained during operation. The filter pad can be made of any type of material, for instance, standard filter paper or cellulose pads and the like and typically is the diameter or length-width of the cartridge in order to separate completely one layer from another layer. A flow diffuser which uniformly diffuses the used dialysate throughout the entire width or diameter of the sorbent cartridge can be used. The flow diffuser can have a design of radial spreading channels made of plastic or other suitable materials. The flow diffuser is typically located prior to any of the optional filter pads or materials used in the sorbent cartridge and is adjacent to the inlet (or part of the inlet) of the sorbent cartridge. A barrier layer(s) can also be used in the sorbent cartridge. A barrier layer can be located between the immobilized enzyme layer and the alumina layer, if present. An example of a barrier layer includes filter paper and the like.

Various overall shapes of the sorbent cartridge include, but are not limited to, a cylindrical shape, rectangular shape, a pyramidal-cylindrical shape as shown, for instance, in FIG. 1 and so on. The shape can be straight-edged or tapered, and so on. Any geometric shape can generally be used. As an option, the PD cartridge has the following dimensions: 2 inches-3 inches diameter by 5 inches to 10 inches length. The HD cartridge can have the following dimensions: 4 inches-6 inches diameter by 6 inches-12 inches long. Other dimensions can be used depending on the needs of the purifying, amount to purify, operating system and the like. Examples of cartridge designs are further shown in U.S. Pat. No. 6,878,283, which is incorporated in its entirety by reference herein. Examples of cartridges are also described in one or more of the patents and/or publications identified herein.

In preparing the Jack Bean meal, the Jack Bean meal can be extracted with a liquid organic solvent, and then the solvent can be evaporated to eliminate organic impurities with the volatiles, and leave intact active urease in the non-evaporated Jack Bean meal residue. The extraction solvent can be, for example, a C1-C4 lower alkyl alcohol such as ethanol, methanol, (iso)propanol, and (iso)butanol, or other liquid organic solvents. Jack Bean meal can be dissolved in ethanol, for example, and then the ethanol can be evaporated to eliminate organic impurities with the volatized fraction and leave an organic, oily residue which contains urease and various higher molecular weight fatty acid derivatives. The evaporation can be promoted by application of heat sufficient to increase volatization without denaturing the urease. The residue can be dried at any temperatures that do not denature the urease, and the resulting dried residue can be used as a purified source of Jack Bean meal and urease remaining therein in a sorbent cartridge, such as an indicated design herein.

As another pretreatment of Jack Bean meal that can be used in the present invention, urease can be extracted from Jack Bean meal by an extraction process and then the urease can be isolated and lyophilized before incorporation into a sorbent cartridge. Methods for extracting urease from Jack Bean meal can be adapted from known methods in this respect, and the urease extracts can be lyophilized and used in sorbent cartridges having designs of the present invention. For example, urease may be extracted from Jack Bean meal through steps including solvent extraction, heat treatment, acid precipitation, and lyophilization. The extraction process may be repeated to increase purity of the urease extract product. For extraction of urease, for example, Jack Bean meal may be mixed with acetone and stirred at about room temperature for one or more minutes. The resulting material can be heated to remove cloudy materials, and urease can be precipitated in the remaining supernatant by adjusting the pH of the solution with acid. The acid precipitated urease can be neutralized to a suitable pH, and then lyophilized before use in a sorbent cartridge.

The cartridges of the present invention, as indicated above, can be used in a variety of separation systems and can be used in the regeneration or purification of dialysates (e.g., HD) or PD solutions. In a less complicated design, spent or used dialysate or PD solutions can simply be passed through one or more cartridges to purify or regenerate the spent fluids. Such a system can be straightforward in setup and can involve merely using a column-type setup wherein the spent fluids are passed from top to bottom wherein gravity permits the spent fluid to go through the cartridge or spent fluid can be passed through the cartridge under pressure which permits the spent fluids to be introduced in any direction. In a more specific system, the system set forth in FIG. 6 can be adapted to use an indicated sorbent cartridge as used especially for hemodialysis; that is a system that can be used as a closed system, or alternatively in a single pass dialysis system (not shown). Such a system permits the continuous reusing of the regenerated dialysate in a patient during dialysis treatment. With respect to a single pass system (not shown), in lieu of discarding the used dialysate to a floor drain, as an alternative, the used dialysis can simply be collected in a container which then can be regenerated or purified by passing the spent dialysate through one or more cartridges as described above.

With respect to peritoneal dialysis, there are several options. First, like hemodialysis, the peritoneal dialysis solution that is spent can be directly passed through one or more cartridges to purify or regenerate the used peritoneal dialysis solution in order to remove the waste products. Alternatively, the peritoneal dialysis solution which is used or spent can first be passed through a dialyzer in the same manner as blood during hemodialysis wherein dialysate removes waste products and the like from the peritoneal dialysis solution and then the dialysate can be regenerated or purified by passing the used or spent dialysate through the cartridge. Either system can be used in the present invention. With a closed PD system the risk of peritonitis can be reduced significantly since the frequent connections which must be made with conventional systems between the catheter in the peritoneal cavity and a succession of dialysis solution containers is avoided in one embodiment of the present invention.

Figure 6:
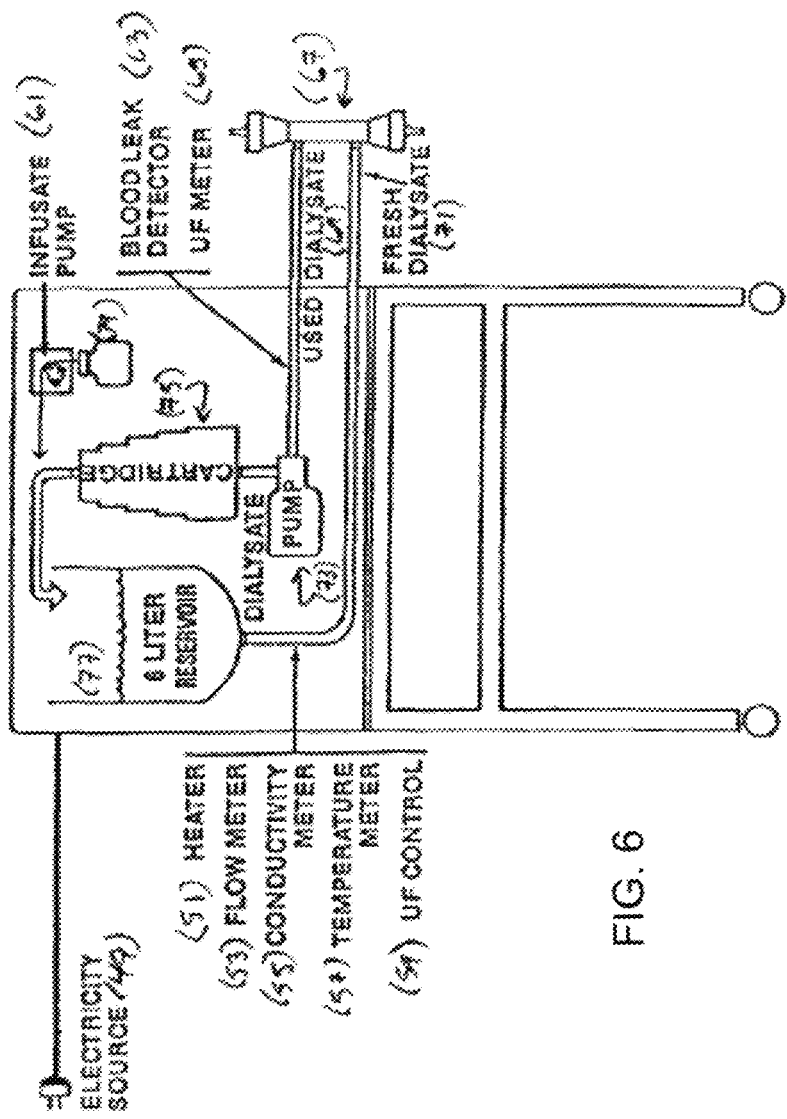
FIG. 6 is a schematic diagram showing a sorbent dialysis system which includes a sorbent cartridge according to an example of the present application.

Referring to FIG. 6, 75 refers to a cartridge, which is a cartridge of the present application. 49 refers to a source of electricity to operate the dialysis system. 51 represents a heater, 53 represents a flow meter, 55 represents a conductivity meter, 57 represents a temperature meter, and 59 represents a UF control. These items are conventional items in a sorbent dialysis system and are known to those skilled in the art and can be used in the present invention. 61 is an infusate pump that is used to pump in fresh concentrate 79 to be mixed with the regenerated dialysate which ultimately enters the reservoir 77 which can be a six liter reservoir. 63 represents a blood leak detector and 65 represents a UF meter which are conventional items in dialysis systems and can be used herein. Component 67 represents a dialyzer. As indicated, a dialyzer is known by those skilled in the art and typically is a system or component that contains a membrane in order to have the waste products pass through the membrane to the dialysate fluid. Similarly, 69 represents used dialysis leaving the dialyzer and 71 represents fresh dialysate entering the dialyzer 67. Component 73 is a pump to pump the used dialysate from the dialyzer into the cartridge 75 which are the cartridges of the present application.

The sorbent cartridges of the present invention can be made for use in multiple hours of dialysis treatment, such as, for example, for up to about 4 hours of dialysis treatment or for up to about 8 hours of dialysis treatment. For example, the 8 hour cartridges can typically be made for home use and the 4 hour cartridges can typically be made for dialysis treatment in medical treatment or dialysis centers. The cartridges of the present invention can generally be used with any type of dialysis system as described above. The flows that pass through the cartridge are typically any conventional flows. For instance, flows from about 50 ml/min or less to 500 ml/min or more of dialysate can flow through the cartridge and can be used in the systems of the present invention. Other flows can be used depending upon the size of the cartridge and the operating system.

The dialysis systems or components thereof described in the above and following patents can be used in the present application and these systems can incorporate the materials and/or cartridges of the present invention: U.S. Pat. Nos. 7,033,498 B2; 8,663,463; 8,597,505; 8,580,112; 8,500,994; 8,366,921; 8,343,346; 8,475,399; and 8,012,118. All of these patents are incorporated in their entirety by reference herein and form a part of the present application.

There are numerous uses for the materials of the present invention and especially the cartridges of the present invention such as the regeneration of dialysis fluids as mentioned above. Furthermore, the cartridges can also be used in any separation process which requires the removal of impurities or waste products from a fluid or other medium that is passable through the materials of the present invention. Also, the present invention may be useful with respect to treating drug overdose patients or other patients which are in need or removing undesirable or dangerous contaminants in a person's blood stream.

Accordingly, the present invention provides useful embodiments that allow the regeneration of dialysate type fluids and other fluids.

The present invention can be used to provide stationary sorbent dialysis systems or portable sorbent dialysis systems. The sorbent dialysis systems can include sorbent hemodialysis, a wearable artificial kidney, sorbent peritoneal dialysis, and other sorbent dialysis systems.

In accordance with other aspects of the present invention, and with no limitation on the layer chemistry, a sorbent cartridge is provided that can include a housing, a first sorbent layer, and a second sorbent layer and optionally one or more other layers. The housing can define a cartridge interior, the cartridge interior having a volume and configured to hold at least two layers of sorbent material. The housing can include a first end having a first port configured to permit entry of a fluid into the cartridge interior, and a second end distal to the first end and having a second port configured to permit exit of the fluid from the cartridge interior. One will appreciate that the present invention need not be dependent on a particular housing or housing configuration, and that the housing is provided as a conventional way to hold and contain various sorbent layers, as well as effluent passing through the layers. The first sorbent layer can be situated in the cartridge interior. The first sorbent layer can have a first geometry and contain a first sorbent material. The second sorbent layer can be situated in the cartridge interior. The second sorbent layer can have a second geometry and can contain a second sorbent material. The first and second sorbent materials can have equivalent chemical compositions. The first geometry can differ from the second geometry in at least one dimension, or the first sorbent material can differ from the second sorbent material in at least one physical characteristic, or both.

The first and second geometries can differ from one another in one or more desired aspects. For example, the first geometry can differ from the second geometry with respect to size, shape, or both. The first sorbent layer can differ from the second sorbent layer in average height, average width, average length, or a combination thereof. The sorbent cartridge can have a central axis about which the first and second sorbent layers are centered, the first sorbent layer and the second sorbent layer are cylindrical, or frusto-conical in shape. The first geometry can differ from the second geometry with respect to average height, average radius, or both. The first sorbent layer and the second sorbent layer can differ in volume, weight, and/or density.

The first sorbent layer and the second sorbent layer can differ in surface area. This surface area difference can be achieved by any desired technique and/or configuration. For example, the volume of the first or second sorbent layer can be greater than the other. Alternatively, or in addition, the size and/or shape of particles can differ between the first and second sorbent layers. The difference in particle size can be a difference in average particle size, whether, mean, median, or mode. Accordingly, the first and second sorbent materials can include particles and average particle size of the first sorbent material differs from average particle size of the second sorbent material. The first and second sorbent materials can include particles and at least one of the first and second sorbent materials can include a particle size not present in the other layer. The first and second sorbent materials can contain one or more particle sizes in common, but still different in average particle size. The first and second sorbent materials can include particles and at least one of the first and second sorbent materials can include a particle shape not present in the other layer. The first and second sorbent materials can contain one or more particle shapes in common, but still different with respect to one or more other particle shapes.

The first sorbent layer and the second sorbent layer can differ in sorbent capacity for at least one species targeted for absorption, adsorption, or both. This difference in sorbent capacity can be accomplished by any desired technique and/or configuration. The difference can be independent of chemistry and can instead be a result of one or more differences in volume, density, particle size, and/or particle shape. The first sorbent layer can have a greater sorbent capacity for at least one species targeted for absorption, adsorption, or both, compared to a sorbent capacity of the second sorbent layer for the at least one species, or vice versa.

The first and second sorbent layers can be positioned with respect to one another in any desired manner. For example, the first sorbent layer can be adjacent to the second sorbent layer. The first and second sorbent layer can be separated from one another by one or more additional layers. The first sorbent layer can be proximal to the first end and the second sorbent layer can be proximal to the second end, or vice versa. The first sorbent layer can at least partially surround the second sorbent layer, or vice versa. That is, a given stratum, cross-sectional volume, of the sorbent cartridge can contain one or more layers. Such layers can have chemical compositions, and the first geometry can differ from the second geometry in at least one dimension, the first sorbent material can differ from the second sorbent material in at least one physical characteristic, or both. For example, the sorbent cartridge can have at least one layer defined by a cross-sectional area with an inner region and outer region wherein the outer region surrounds the inner region, and the layer is defined by a height. The first and second sorbent layers can have the same average height with respect to an axial dimension between the first and second ends, and differ with respect to average width, average length, or both. The first and second sorbent layers can be concentric and positioned about a central axis along the axial dimension, the first sorbent layer having a width defined by a first radius extending from the central axis to the second sorbent layer, and the second sorbent layer having a width defined by the difference of the first radius and a second radius greater than the first radius. The sorbent layers can share a common axis, but have geometries that are not circular or even not curvilinear. For example, the geometries can be rectilinear. Circular or other curvilinear geometric layers need not share a common axis, and can be offset from one another with respect to a particular axis of the sorbent cartridge.

With respect to the difference between the first geometry and the second geometry, this difference with respect to size, shape, or both can be a difference of 5% or more, 10% or more, 15% or more, 20% or more, 50% or more, 100% or more, 200% or more, and the like. For instance, the difference can be from about 5% to about 200% with respect to size, shape, or both. Put another way, the comparison of the first sorbent layer and the second sorbent layer with respect to average height, average width, average length or any combination thereof can vary by these percents.

Further, with regard to comparing the first sorbent layer with the second sorbent layer with regard to volume, average density, particle size, (e.g., average particle size), and similar parameters, the difference between the first sorbent layer and the second sorbent layer can vary by these percents as set forth above.

The sorbent cartridge can include at least one additional sorbent layer including a sorbent material having a chemical composition differing from the chemical compositions of the first and second sorbent materials. The at least one additional sorbent layer can be located between the first end and first sorbent layer, between the first and second sorbent layers, or between the second sorbent layer and the second end. The first sorbent layer and the second sorbent layer can be separated from one another by at least one intervening layer including a third sorbent layer having a third geometry and including a third sorbent material, wherein the third sorbent material has a chemical composition non-equivalent to the chemical composition of the first and second sorbent layers. The first sorbent layer and the second sorbent layer can be separated from one another by at least one intervening layer including a third sorbent layer having a third geometry and include a third sorbent material. The first, second, and third sorbent materials can have equivalent chemical compositions, and the third geometry can differ from the first and second geometries, and/or the third sorbent material can differ from the first and second sorbent materials in at least one physical characteristic, and/or the third geometry can differ from either the first geometry or the second geometry as well as differing from either the first sorbent material or the second sorbent material in at least one physical property.

The first and second sorbent materials can have substantially the same or identical chemical compositions. The first and second sorbent materials can have equivalent chemical compositions. For example, the first and second sorbent material can both be cation exchangers, or can both be anion exchangers. The first and second sorbent materials can include at least one cation exchanger. The first and second sorbent materials can include the same cation exchanger. Any desired cation exchanger can be used. For example, the cation exchanger can include zirconium phosphate. The first and second sorbent layers can have the same cation exchange capacity, with respect to one or more types of cations. The first sorbent layer can have a greater cation exchange capacity than the second sorbent layer, or vice versa, with respect to one or more types of cations. The first and second sorbent materials can include at least one anion exchanger. The first and second sorbent materials can include the same anion exchanger. Any desired anion exchanger can be used. For example, the anion exchanger can contain hydrous zirconium oxide. The first and second sorbent layers can have the same anion exchange capacity with respect to one or more types of anion. The first sorbent layer can have a greater anion exchange capacity than the second sorbent layer, or vice versa, with respect to one or more types of anions.

The first and second sorbent materials can include urease, for example, in the form of a Jack Bean paste. The urease in the two different layers can be substantially the same or identical, and can be obtained from such sources as jack beans (for example, *Canavalia ensiformis*), yeasts, and bacteria (for example, *Bacillus pasteurii*). Any urease or combination of ureases can be employed. The urease can differ in specific activity between the two layers. The urease can differ in biological source. The urease can be isolated from a natural source or recombinant.

The first and second sorbent materials can include activated carbon. The activated carbon in the two layers can differ in the degree of activation, and/or both layers can contain non-activated carbon. The type of activated carbon in the two layers can be substantially the same or identical. The layers can share one or more types of activated carbon, but can differ with respect to one or more types of activated carbon. Any type or combination of types of activated carbon can be employed. The carbon can be chemically and/or physically activated. Any desired grade of activated carbon can be used. Examples of activated carbon include powdered activated carbon, granular activated carbon, bead activated carbon, extruded activated carbon, impregnated carbon, polymer-coated carbon, or any combination thereof. Activated carbon can differ with respect to porosity, specific surface area, and/or texture characteristics.

The present invention provides a sorbent cartridge having an inlet and outlet including at least a first layer and a second layer. The first layer and the second layer can contain particulate material having substantially the same or identical chemical composition. The first layer can be located closer to the inlet than the second layer. The particulate material in the first layer can have at least a greater/higher property then the particulate material in the second layer with respect to average particle size, average surface area, adsorption capacity, or any combination thereof for at least one species.

Non-limiting examples of sorbent cartridges are discussed as follows. Each of these examples can include a housing that surrounds all or a portion of the sorbent layers. The housing can conform to the shape of the sorbent layers in whole or part, or can be independent of the sorbent layer profile. Sorbent layers can be formed using any desired technique. For example, solid molds or hollow frames can be used to form the various strata (horizontal slices) and sorbent layers of a given sorbent cartridge. Sorbent layers of a given stratum can be formed simultaneously or in stages, for example, for successive concentric or nested sorbent layers. Adjacent sorbent layers can have sharp, distinct, blurred, and/or transitioned boundaries. Sorbent layers can contain gradients of sorbent material with respect to density, surface area, composition, and/or any other desired characteristic or combination of characteristics. The shape, size, order, and/or number of the strata and/or layers can vary as desired. Sorbent layers and/or strata can include any shapes or combination of shapes, curvilinear and/or rectilinear, for example, cones, cylinders, conical frustums, polygonal (regular and/or irregular) frustums, cylindrical prisms, conical prisms, polygonal (regular and/or irregular) prisms, and the like. The sides of a sorbent cartridge can be continuous or discontinuous, smooth or stepped, or a combination thereof; a description of one is understood to be representative of the other. Descriptions of square embodiments are also representative of rhombic, rectangular, regular polygonal, and irregular polygonal embodiments, and the like. Any two or more sorbent layers can have equivalent chemical compositions, but differ in respect to geometry and/or physical characteristic. While strata generally refer to horizontal slices, other orientations are also encompassed by the present invention.

The present invention includes the following aspects/embodiments/features in any order and/or in any combination:

1. The present invention relates to a sorbent cartridge comprising:
    a) a first carbon-containing layer;
    b) an enzyme-comprising layer that follows the first carbon-containing layer within the sorbent cartridge;
    c) a second carbon-containing layer that follows the enzyme-comprising layer within the sorbent cartridge;
    d) a zirconium phosphate-containing layer that follows the second carbon-containing layer within the sorbent cartridge;
    e) a hydrous zirconium oxide layer that follows the zirconium phosphate-containing layer comprising hydrous zirconium oxide-chloride having an alkaline pH; and
    f) a (bi)carbonate layer that follows the hydrous zirconium oxide layer comprising sodium (bi)carbonate.
2. The sorbent cartridge of any preceding or following embodiment/feature/aspect, wherein the hydrous zirconium oxide-chloride has a pH greater than about 8.
3. The sorbent cartridge of any preceding or following embodiment/feature/aspect, wherein the hydrous zirconium oxide-chloride has a pH greater than about 9.
4. The sorbent cartridge of any preceding or following embodiment/feature/aspect, wherein the hydrous zirconium oxide-chloride has a pH of from about 9.5 to about 10.5.
5. The sorbent cartridge of any preceding or following embodiment/feature/aspect, wherein the (bi)carbonate layer that follows the hydrous zirconium oxide layer comprising $NaHCO_3$.
6. The sorbent cartridge of any preceding or following embodiment/feature/aspect, wherein the hydrous zirconium oxide layer is free of acetate.
7. The sorbent cartridge of any preceding or following embodiment/feature/aspect, wherein the first carbon-containing layer is a layer of granular activated carbon or a carbon pad, and the second carbon-containing layer is a layer of granular activated carbon or a carbon pad.
8. The sorbent cartridge of any preceding or following embodiment/feature/aspect, wherein the enzyme-comprising layer comprises a Jack Bean meal/alumina blend.
9. The sorbent cartridge of any preceding or following embodiment/feature/aspect, further comprising an alumina-containing layer between the enzyme-containing layer and the second carbon-containing layer.
10. The present invention relates to a method to regenerate or purify spent dialysis fluid comprising passing spent dialysis fluid through the sorbent cartridge of any preceding or following embodiment/feature/aspect.
11. The method of any preceding or following embodiment/feature/aspect, wherein said (bi)carbonate layer is dissolved by the passing dialysis fluid.
12. The present invention relates to a dialysis system to regenerate or purify spent dialysis fluid comprising the sorbent cartridge of any preceding or following embodiment/feature/aspect.
13. The present invention relates to a sorbent cartridge comprising:
    a) a first carbon-containing layer;
    b) an enzyme-comprising layer that follows the first carbon-containing layer within the sorbent cartridge;
    c) a second carbon-containing layer that follows the enzyme-comprising layer within the sorbent cartridge;
    d) a zirconium phosphate-containing layer that follows the second carbon-containing layer within the sorbent cartridge, wherein the zirconium phosphate-containing layer comprises sodium loading of greater than 55 mg Na/g zirconium phosphate;
    e) a hydrous zirconium oxide layer that follows the zirconium phosphate-containing layer comprising hydrous zirconium oxide-chloride having an alkaline pH; and
    f) a (bi)carbonate layer that follows the hydrous zirconium oxide layer comprising sodium (bi)carbonate.
14. The sorbent cartridge of any preceding or following embodiment/feature/aspect, wherein the zirconium phosphate-containing layer comprises sodium loading of about 56 to about 58 mg Na/g zirconium phosphate.
15. The sorbent cartridge of any preceding or following embodiment/feature/aspect, wherein the zirconium phosphate-containing layer comprises sodium loading of about 57 mg Na/g zirconium phosphate.

16. The sorbent cartridge of any preceding or following embodiment/feature/aspect, wherein the hydrous zirconium oxide-chloride has a pH greater than about 8.
17. The sorbent cartridge of any preceding or following embodiment/feature/aspect, wherein the hydrous zirconium oxide-chloride has a pH greater than about 9.
18. The sorbent cartridge of any preceding or following embodiment/feature/aspect, wherein the hydrous zirconium oxide-chloride has a pH of from about 9.5 to about 10.5.
19. The sorbent cartridge of any preceding or following embodiment/feature/aspect, wherein the (bi)carbonate layer comprising sodium bicarbonate.
20. The sorbent cartridge of any preceding or following embodiment/feature/aspect, wherein the first carbon-containing layer is a layer of granular activated carbon or a carbon pad, and the second carbon-containing layer is a layer of granular activated carbon or a carbon pad.
21. The sorbent cartridge of any preceding or following embodiment/feature/aspect, wherein the enzyme-comprising layer comprises a Jack Bean meal/alumina blend.
22. The sorbent cartridge of any preceding or following embodiment/feature/aspect, further comprising an alumina-containing layer between the enzyme-comprising layer and the second carbon-containing layer.
23. The present invention relates to a method to regenerate or purify spent dialysis fluid comprising passing spent dialysis fluid through the sorbent cartridge of any preceding or following embodiment/feature/aspect.
24. The present invention relates to a dialysis system to regenerate or purify spent dialysis fluid comprising the sorbent cartridge of any preceding or following embodiment/feature/aspect.
25. A sorbent cartridge having an inlet and outlet comprising at least a first layer and a second layer, wherein said first layer and said second layer comprise particulate material having the same or substantially the same chemical composition and wherein said first layer is located closer to said inlet than second layer and wherein said particulate material in said first layer has at least a greater/higher property than said particulate material from said second layer with respect to a) average particle size, b) average surface area, and/or c) adsorption capacity for at least one species.
26. A sorbent cartridge comprising:
    a housing
    defining a cartridge interior, the cartridge interior having a volume and configured to hold at least two layers of sorbent material, and
    comprising a first end comprising a first port configured to permit entry of a fluid into the cartridge interior, and a second end distal to the first end and comprising a second port configured to permit exit of the fluid from the cartridge interior;
    a first sorbent layer situated in the cartridge interior, the first sorbent layer having a first geometry and comprising a first sorbent material; and
    a second sorbent layer situated in the cartridge interior, the second sorbent layer having a second geometry and comprising a second sorbent material;
    wherein the first and second sorbent materials have equivalent chemical compositions, and (a) the first geometry differs from the second geometry in at least one dimension, (b) the first sorbent material differs from the second sorbent material in at least one physical characteristic, or (c) both.
27. The sorbent cartridge of any preceding or following embodiment/feature/aspect, wherein the first geometry differs from the second geometry.
28. The sorbent cartridge of any preceding or following embodiment/feature/aspect, wherein the first geometry differs from the second geometry in respect to size, shape, or both.
29. The sorbent cartridge of any preceding or following embodiment/feature/aspect, wherein the first sorbent layer differs from the second sorbent layer in average height, average width, average length, or a combination thereof.
30. The sorbent cartridge of any preceding or following embodiment/feature/aspect, wherein the sorbent cartridge has a central axis about which the first and second sorbent layers are centered, the first sorbent layer and the second sorbent layer are cylindrical, or frusto-conical in shape, and the first geometry differs from the second geometry in respect to average height, average radius, or both.
31. The sorbent cartridge of any preceding or following embodiment/feature/aspect, wherein the first sorbent layer and the second sorbent layer differ in volume.
32. The sorbent cartridge of any preceding or following embodiment/feature/aspect, wherein the first sorbent layer and the second sorbent layer differ in average density.
33. The sorbent cartridge of any preceding or following embodiment/feature/aspect, wherein the first sorbent layer and the second sorbent layer differ in surface area.
34. The sorbent cartridge of any preceding or following embodiment/feature/aspect, wherein the first sorbent layer and the second sorbent layer differ in sorbent capacity for at least one species targeted for absorption, adsorption, or both.
35. The sorbent cartridge of any preceding or following embodiment/feature/aspect, wherein the first and second sorbent materials comprise particles and average particle size of the first sorbent material differs from average particle size of the second sorbent material.
36. The sorbent cartridge of any preceding or following embodiment/feature/aspect, wherein the first and second sorbent materials comprise particles and at least one of the first and second sorbent materials comprises a particle shape not present in the other layer.
37. The sorbent cartridge of any preceding or following embodiment/feature/aspect, wherein the first sorbent layer at least partially surrounds the second sorbent layer, or vice versa.
38. The sorbent cartridge of any preceding or following embodiment/feature/aspect, wherein the first and second sorbent layers have the same average height with respect to an axial dimension between the first and second ends, and differ in respect to average width, average length, or both.
39. The sorbent cartridge of any preceding or following embodiment/feature/aspect, wherein the first and second sorbent layers are concentric and positioned about a central axis along the axial dimension, the first sorbent layer having a width defined by a first radius extending from the central axis to the second sorbent layer, and the second sorbent layer having a width defined by the difference of the first radius and a second radius greater than the first radius.
40. The sorbent cartridge of any preceding or following embodiment/feature/aspect having at least one layer defined by a cross-sectional area with an inner region and outer region wherein the outer region surrounds the inner region, and the layer is defined by a height.

41. The sorbent cartridge of any preceding or following embodiment/feature/aspect, wherein the first sorbent layer is adjacent to the second sorbent layer.
42. The sorbent cartridge of any preceding or following embodiment/feature/aspect, wherein the first sorbent layer is proximal the first end and the second sorbent layer is proximal the second end.
43. The sorbent cartridge of any preceding or following embodiment/feature/aspect, wherein the first sorbent layer has a greater sorbent capacity for at least one species targeted for absorption, adsorption, or both, compared to a sorbent capacity of the second sorbent layer for the at least one species.
44. The sorbent cartridge of any preceding or following embodiment/feature/aspect, further comprising at least one additional sorbent layer comprising a sorbent material having a chemical composition differing from the chemical compositions of the first and second sorbent materials.
45. The sorbent cartridge of any preceding or following embodiment/feature/aspect, wherein the at least one additional sorbent layer is located between the first end and first sorbent layer, between the first and second sorbent layers, or between the second sorbent layer and the second end.
46. The sorbent cartridge of any preceding or following embodiment/feature/aspect, wherein the first sorbent layer and the second sorbent layer are separated from one another by at least one intervening layer comprising a third sorbent layer having a third geometry and comprising a third sorbent material, wherein the third sorbent material has a chemical composition non-equivalent to the chemical composition of the first and second sorbent layers.
47. The sorbent cartridge of any preceding or following embodiment/feature/aspect, wherein first sorbent layer and the second sorbent layer are separated from one another by at least one intervening layer comprising a third sorbent layer having a third geometry and comprising a third sorbent material, wherein the first, second, and third sorbent materials have equivalent chemical compositions, and (a) the third geometry differs from the first and second geometries, (b) the third sorbent material differs from the first and second sorbent materials in at least one physical characteristic, or (c) the third geometry differs from either the first geometry or the second geometry and the third sorbent material differs from either the first sorbent material or the second sorbent material in at least one physical property.
48. The sorbent cartridge of any preceding or following embodiment/feature/aspect, wherein the first and second sorbent materials have identical chemical compositions.
49. The sorbent cartridge of any preceding or following embodiment/feature/aspect, wherein the first and second sorbent materials comprise at least one cation exchanger.
50. The sorbent cartridge of any preceding or following embodiment/feature/aspect, wherein the first and second sorbent materials comprise the same cation exchanger.
51. The sorbent cartridge of any preceding or following embodiment/feature/aspect, wherein the cation exchanger comprises zirconium phosphate.
52. The sorbent cartridge of any preceding or following embodiment/feature/aspect, wherein the first sorbent layer has a greater cation exchange capacity than the second sorbent layer.
53. The sorbent cartridge of any preceding or following embodiment/feature/aspect, wherein the first and second sorbent materials comprise at least one anion exchanger.
54. The sorbent cartridge of any preceding or following embodiment/feature/aspect, wherein the first and second sorbent materials comprise the same anion exchanger.
55. The sorbent cartridge of any preceding or following embodiment/feature/aspect, wherein the anion exchanger comprises hydrous zirconium oxide.
56. The sorbent cartridge of any preceding or following embodiment/feature/aspect, wherein the anion exchanger further comprises zirconium carbonate.
57. The sorbent cartridge of any preceding or following embodiment/feature/aspect, wherein the first sorbent layer has a greater anion exchange capacity than the second sorbent layer.
58. The sorbent cartridge of any preceding or following embodiment/feature/aspect, wherein the first and second sorbent materials comprise urease.
59. The sorbent cartridge of any preceding or following embodiment/feature/aspect, wherein the first and second sorbent materials comprise activated carbon.
60. A sorbent cartridge having an inlet and outlet comprising at least a first layer and a second layer, wherein the first layer and the second layer comprise particulate material having substantially the same chemical composition and wherein the first layer is located closer to the inlet than the second layer and wherein the particulate material in the first layer has at least a greater/higher property then the particulate material in the second layer with respect to a) average particle size, b) average surface area, and/or c) adsorption capacity for at least one species.
61. The present invention relates to a sorbent cartridge comprising:
    a) a first carbon-containing layer;
    b) an enzyme-containing layer comprising Jack Bean meal that follows the first carbon-containing layer within the sorbent cartridge;
    c) a second carbon-containing layer that follows the enzyme-containing layer within the sorbent cartridge; and
    d) a first zirconium phosphate-containing layer that follows the second carbon-containing layer within the sorbent cartridge.
62. The sorbent cartridge of any preceding or following embodiment/feature/aspect, wherein the first carbon-containing layer is a layer of granular activated carbon or a carbon pad, and the second carbon-containing layer is a layer of granular activated carbon or a carbon pad.
63. The sorbent cartridge of any preceding or following embodiment/feature/aspect, wherein the enzyme-containing layer comprises Jack Bean meal/alumina blend.
64. The sorbent cartridge of any preceding or following embodiment/feature/aspect, further comprising an alumina-containing layer between the enzyme-containing layer and the second carbon-containing layer.
65. The present invention relates to a method of making a sorbent cartridge, comprising:
    a) dissolving Jack Bean meal containing organic impurities in an organic solvent;
    b) evaporating the organic solvent and at least a portion of the organic impurities as volatiles to separate the volatiles from a non-volatized residue comprising urease;
    c) drying the residue comprising urease to provide dry urease-containing material; and
    d) incorporating the dry urease-containing material between carbon-containing layers in a sorbent cartridge that includes zirconium phosphate without a layer of zirconium phosphate being between either of the carbon-containing layers and the dry urease-containing material.

The present invention can include any combination of these various features or embodiments above and/or below as set forth in sentences and/or paragraphs. Any combination of disclosed features herein is considered part of the present invention and no limitation is intended with respect to combinable features.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

It will be apparent to those skilled in the art that various modifications and variations can be made to the embodiments of the present invention without departing from the spirit or scope of the present invention. Thus, it is intended that the present invention covers other modifications and variations of this invention provided they come within the scope of the appended claims and their equivalents.

What is claimed is:

1. A sorbent cartridge, comprising from inlet to outlet:
   a) a first carbon-containing layer;
   b) an enzyme-comprising layer that follows the first carbon-containing layer within the sorbent cartridge;
   c) a second carbon-containing layer that follows the enzyme-comprising layer within the sorbent cartridge;
   d) a zirconium phosphate-containing layer that follows the second carbon-containing layer within the sorbent cartridge;
   e) a hydrous zirconium oxide layer that follows the zirconium phosphate-containing layer comprising hydrous zirconium oxide-chloride having an alkaline pH; and
   f) a (bi)carbonate layer that follows the hydrous zirconium oxide layer comprising sodium (bi)carbonate.

2. The sorbent cartridge of claim 1, wherein the hydrous zirconium oxide-chloride has a pH greater than about 8.

3. The sorbent cartridge of claim 1, wherein the hydrous zirconium oxide-chloride has a pH greater than about 9.

4. The sorbent cartridge of claim 1, wherein the hydrous zirconium oxide-chloride has a pH of from about 9.5 to about 10.5.

5. The sorbent cartridge of claim 1, wherein the (bi)carbonate layer that follows the hydrous zirconium oxide layer comprising $NaHCO_3$.

6. The sorbent cartridge of claim 1, wherein the hydrous zirconium oxide layer is free of acetate.

7. The sorbent cartridge of claim 1, wherein the first carbon-containing layer is a layer of granular activated carbon or a carbon pad, and the second carbon-containing layer is a layer of granular activated carbon or a carbon pad.

8. The sorbent cartridge of claim 1, wherein the enzyme-comprising layer comprises a Jack Bean meal/alumina blend.

9. The sorbent cartridge of claim 1, further comprising an alumina-containing layer between the enzyme-comprising layer and the second carbon-containing layer.

10. A method to regenerate or purify dialysis fluid comprising passing dialysis fluid through the sorbent cartridge of claim 1.

11. The method of claim 10, wherein said (bi)carbonate layer is dissolved by the passing dialysis fluid.

12. A dialysis system to regenerate or purify spent dialysis fluid comprising the sorbent cartridge of claim 1.

13. The sorbent cartridge of claim 1 comprising:
   a housing
      defining a cartridge interior, the cartridge interior having a volume and configured to hold at least two layers of sorbent material, and
      comprising a first end comprising a first port configured to permit entry of a fluid into the cartridge interior, and a second end distal to the first end and comprising a second port configured to permit exit of the fluid from the cartridge interior;
   a first sorbent layer situated in the cartridge interior, the first sorbent layer having a first geometry and comprising a first sorbent material; and
   a second sorbent layer situated in the cartridge interior, the second sorbent layer having a second geometry and comprising a second sorbent material;
   wherein the first and second sorbent materials have equivalent chemical compositions, and (a) the first geometry differs from the second geometry in at least one dimension, (b) the first sorbent material differs from the second sorbent material in at least one physical characteristic, or (c) both, and
   wherein the first and second sorbent materials are selected from said carbon-containing layer, said enzyme-comprising layer, said zirconium phosphate-containing layer, said hydrous zirconium oxide layer or any combination thereof.

14. The sorbent cartridge of claim 13, wherein the first geometry differs from the second geometry.

15. The sorbent cartridge of claim 14, wherein the first geometry differs from the second geometry in respect to size, shape, or both.

16. The sorbent cartridge of claim 14, wherein the first sorbent layer differs from the second sorbent layer in average height, average width, average length, or a combination thereof.

17. The sorbent cartridge of claim 14, wherein the sorbent cartridge has a central axis about which the first and second sorbent layers are centered, the first sorbent layer and the second sorbent layer are cylindrical, or frusto-conical in shape, and the first geometry differs from the second geometry in respect to average height, average radius, or both.

18. The sorbent cartridge of claim 14, wherein the first and second sorbent layers are concentric and positioned about a central axis along the axial dimension, the first sorbent layer having a width defined by a first radius extending from the central axis to the second sorbent layer, and the second sorbent layer having a width defined by the difference of the first radius and a second radius greater than the first radius.

19. The sorbent cartridge of claim 13, wherein the first sorbent layer and the second sorbent layer differ in volume.

20. The sorbent cartridge of claim 13, wherein the first sorbent layer and the second sorbent layer differ in average density.

21. The sorbent cartridge of claim 13, wherein the first sorbent layer and the second sorbent layer differ in surface area.

22. The sorbent cartridge of claim 13, wherein the first sorbent layer and the second sorbent layer differ in sorbent capacity for at least one species targeted for absorption, adsorption, or both.

23. The sorbent cartridge of claim 13, wherein the first and second sorbent materials comprise particles and average particle size of the first sorbent material differs from average particle size of the second sorbent material.

24. The sorbent cartridge of claim 13, wherein the first and second sorbent materials comprise particles and at least one of the first and second sorbent materials comprises a particle shape not present in the other layer.

25. The sorbent cartridge of claim 13, wherein the first sorbent layer at least partially surrounds the second sorbent layer, or vice versa.

26. The sorbent cartridge of claim 13, wherein the first and second sorbent layers have the same average height with respect to an axial dimension between the first and second ends, and differ in respect to average width, average length, or both.

27. The sorbent cartridge of claim 13 having at least one layer defined by a cross-sectional area with an inner region and outer region wherein the outer region surrounds the inner region, and the layer is defined by a height.

28. The sorbent cartridge of claim 13, wherein the first sorbent layer is adjacent to the second sorbent layer.

29. The sorbent cartridge of claim 13, wherein the first sorbent layer is proximal the first end and the second sorbent layer is proximal the second end.

30. The sorbent cartridge of claim 13, wherein the first sorbent layer has a greater sorbent capacity for at least one species targeted for absorption, adsorption, or both, compared to a sorbent capacity of the second sorbent layer for the at least one species.

31. The sorbent cartridge of claim 13, further comprising at least one additional sorbent layer comprising a sorbent material having a chemical composition differing from the chemical compositions of the first and second sorbent materials.

32. The sorbent cartridge of claim 13, wherein the at least one additional sorbent layer is located between the first end and first sorbent layer, between the first and second sorbent layers, or between the second sorbent layer and the second end.

33. The sorbent cartridge of claim 13, wherein the first sorbent layer and the second sorbent layer are separated from one another by at least one intervening layer comprising a third sorbent layer having a third geometry and comprising a third sorbent material, wherein the third sorbent material has a chemical composition non-equivalent to the chemical composition of the first and second sorbent layers.

34. The sorbent cartridge of claim 13, wherein first sorbent layer and the second sorbent layer are separated from one another by at least one intervening layer comprising a third sorbent layer having a third geometry and comprising a third sorbent material, wherein the first, second, and third sorbent materials have equivalent chemical compositions, and (a) the third geometry differs from the first and second geometries, (b), the third sorbent material differs from the first and second sorbent materials in at least one physical characteristic, or (c) the third geometry differs from either the first geometry or the second geometry and the third sorbent material differs from either the first sorbent material or the second sorbent material in at least one physical property.

35. The sorbent cartridge of claim 13, wherein the first and second sorbent materials have identical chemical compositions.

36. The sorbent cartridge of claim 13, wherein the first and second sorbent materials comprise at least one cation exchanger.

37. The sorbent cartridge of claim 36, wherein the first and second sorbent materials comprise the same cation exchanger.

38. The sorbent cartridge of claim 37, wherein the cation exchanger comprises zirconium phosphate.

39. The sorbent cartridge of claim 36, wherein the first sorbent layer has a greater cation exchange capacity than the second sorbent layer.

40. The sorbent cartridge of claim 13, wherein the first and second sorbent materials comprise at least one anion exchanger.

41. The sorbent cartridge of claim 40, wherein the first and second sorbent materials comprise the same anion exchanger.

42. The sorbent cartridge of claim 41, wherein the anion exchanger comprises hydrous zirconium oxide.

43. The sorbent cartridge of claim 42, wherein the anion exchanger further comprises zirconium carbonate.

44. The sorbent cartridge of claim 40, wherein the first sorbent layer has a greater anion exchange capacity than the second sorbent layer.

45. The sorbent cartridge of claim 13, wherein the first and second sorbent materials comprise urease.

46. The sorbent cartridge of claim 13, wherein the first and second sorbent materials comprise activated carbon.

47. The sorbent cartridge of claim 1 having an inlet and outlet comprising at least a first layer and a second layer, wherein the first layer and the second layer comprise particulate material having the same or substantially the same chemical composition and wherein the first layer is located closer to the inlet than the second layer and wherein the particulate material in the first layer has at least a greater/higher property then the particulate material in the second layer with respect to a) average particle size, b) average surface area, or c) adsorption capacity for at least one species, wherein the first layer and second layer are selected from said carbon-containing layer, said enzyme-comprising layer, said zirconium phosphate-containing layer, said hydrous zirconium oxide layer and the combination thereof.

48. A method of making the sorbent cartridge of claim 1, wherein said enzyme-comprising layer contains urease, said method comprising:
   a) dissolving Jack Bean meal containing organic impurities in an organic solvent;
   b) evaporating the organic solvent and at least a portion of the organic impurities as volatiles to separate the volatiles from a non-volatized residue comprising urease;
   c) drying the residue comprising urease to provide dry urease-containing material; and
   d) incorporating the dry urease-containing material between carbon-containing layers in a sorbent cartridge that includes zirconium phosphate without a layer of zirconium phosphate being between either of the carbon-containing layers and the dry urease-containing material.

49. A sorbent cartridge comprising from inlet to outlet:
   a) a first carbon-containing layer;
   b) an enzyme-comprising layer that follows the first carbon-containing layer within the sorbent cartridge;
   c) a second carbon-containing layer that follows the enzyme-comprising layer within the sorbent cartridge;

d) a zirconium phosphate-containing layer that follows the second carbon-containing layer within the sorbent cartridge, wherein the zirconium phosphate-containing layer comprises sodium loading of greater than 55 mg Na/g zirconium phosphate;
e) a hydrous zirconium oxide layer that follows the zirconium phosphate-containing layer comprising hydrous zirconium oxide-chloride having an alkaline pH; and
f) a (bi)carbonate layer that follows the hydrous zirconium oxide layer comprising sodium (bi)carbonate.

50. The sorbent cartridge of claim 49, wherein the zirconium phosphate-containing layer comprises sodium loading of about 56 to about 58 mg Na/g zirconium phosphate.

51. The sorbent cartridge of claim 49, wherein the zirconium phosphate-containing layer comprises sodium loading of about 57 mg Na/g zirconium phosphate.

52. The sorbent cartridge of claim 49, wherein the hydrous zirconium oxide-chloride has a pH greater than about 8.

53. The sorbent cartridge of claim 49, wherein the hydrous zirconium oxide-chloride has a pH greater than about 9.

54. The sorbent cartridge of claim 49, wherein the hydrous zirconium oxide-chloride has a pH of from about 9.5 to about 10.5.

55. The sorbent cartridge of claim 49, wherein the (bi)carbonate layer comprising sodium bicarbonate.

56. The sorbent cartridge of claim 49, wherein the first carbon-containing layer is a layer of granular activated carbon or a carbon pad, and the second carbon-containing layer is a layer of granular activated carbon or a carbon pad.

57. The sorbent cartridge of claim 49, wherein the enzyme-comprising layer comprises a Jack Bean meal/alumina blend.

58. The sorbent cartridge of claim 49, further comprising an alumina-containing layer between the enzyme-comprising layer and the second carbon-containing layer.

59. A method to regenerate or purify spent dialysis fluid comprising passing spent dialysis fluid through the sorbent cartridge of claim 49.

60. A dialysis system to regenerate or purify spent dialysis fluid comprising the sorbent cartridge of claim 49.

* * * * *